United States Patent [19]

Van Daele et al.

[11] Patent Number: 4,990,521

[45] Date of Patent: Feb. 5, 1991

[54] 4-(AROYLAMINO)PIPERIDINE-BUTANI-MIDE DERIVATIVES

[75] Inventors: Georges H. P. Van Daele, Turnhout; Freddy F. Vlaeminck, Lille; Francois M. Sommen, Wortel; Michel A. J. De Cleyn, Merksplas, all of Belgium

[73] Assignee: Janssen Pharmaceutica, Beerse, Belgium

[21] Appl. No.: 405,575

[22] Filed: Sep. 8, 1989

Related U.S. Application Data

[63] Continuation of Ser. No. 57,451, May 26, 1987, abandoned, which is a continuation-in-part of Ser. No. 882,067, Jul. 3, 1986, abandoned.

[51] Int. Cl.$^5$ .............................................. A61K 31/445
[52] U.S. Cl. ..................... 514/327; 514/235.5; 514/316; 514/318; 514/326; 514/867
[58] Field of Search ................................. 514/316, 327

[56] References Cited

U.S. PATENT DOCUMENTS

| | | | |
|---|---|---|---|
| 3,647,805 | 3/1972 | Irikura et al. | 514/927 |
| 3,714,159 | 1/1973 | Janssen et al. | 260/247.1 |
| 4,069,331 | 1/1978 | Langbein et al. | 514/329 |
| 4,138,492 | 2/1979 | Noverola et al. | 514/316 |

FOREIGN PATENT DOCUMENTS 76530 12/1985 European Pat. Off. .

OTHER PUBLICATIONS

*Chemical Abstracts*, vol. 99 (1983), 194812d.

*Primary Examiner*—Frederick E. Waddell
*Attorney, Agent, or Firm*—Charles J. Metz

[57] ABSTRACT

A method of treating warm-blooded animals suffering from diarrhea, which method comprises the administration of particular 4-(aroylamino)piperidinebutanamide derivatives and compositions containing the same. Novel 4-(aroylamino)piperidinebutanamide derivatives.

15 Claims, No Drawings

4-(AROYLAMINO)PIPERIDINE-BUTANIMIDE DERIVATIVES

CROSS-REFERENCE TO RELATED APPLICATIONS

This is a continuation of application Ser. No. 57,451, filed May 26, 1987, which is a continuation-in-part of our co-pending application Ser. No. 882,067, filed July 3, 1986, now abandoned.

BACKGROUND OF THE INVENTION

The present invention is concerned with antidiarrheal agents, pharmaceutical compositions containing these agents and methods of treating warm-blooded animals suffering from diarrhea.

Diarrhea is one of the most common disorders. In many parts of the world, diarrhea produces more illness and kills more infants and children than all other diseases combined. Effective treatment of diarrhea may therefore save more lives and relieve more inconvenience than generally is recognized.

The present invention concerns the useful antidiarrheal properties of a number of 4-(aroylamino)-piperidinebutanamide derivatives and their use in the treatment of diarrhea.

Some of the 4-(aroylamino)piperidinebutanamide derivatives of the present invention are known from the Published European Patent Application No. 0,076,530 which corresponds to U.S. Application Ser. No. 362,814, while others are new.

In the U.S. Pat. Nos. 3,547,805, 4,069,331 and 4,138,492 there are described a number of N-piperidinylbenzamides bearing a substituent in the 1-position of the piperidine ring a compounds being useful in the treatment of gastric ulcers, psychic disorders and migraine and as anti-emetics.

DESCRIPTION OF THE PREFERRED EMBODIMENTS

The present invention is concerned with a method of treating blooded animals suffering from diarrhea. which method comprises the systemic administration to warm-blooded animals of an amount effective in treating diarrhea of compound having the formula:

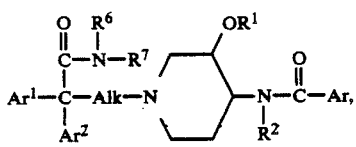

(I)

the N-oxide forms, the pharmaceutically acceptable acid-addition salts and possible stereoisomeric forms thereof, wherein $R^1$ is a member selected from the group consisting of hydrogen, $C_{1-6}$alkyl, aryl$C_{1-6}$alkyl, $C_{1-6}$alkylcarbonyl, amino$C_{1-6}$alkyl and mono- and di($C_{1-6}$alkyl)amino$C_{1-6}$alkyl;

$R_2$ is a member selected from the group consisting of hydrogen and $C_{1-6}$alkyl;

Ar is thienyl, halothienyl, furanyl, halofuranyl, pyridinyl, aminopyridinyl, thiazolyl, imidazolyl or a radical of formula

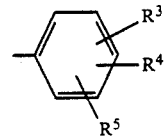

(a-1)

wherein $R^3$, $R^4$ and $R^5$ are each independently selected from the group consisting of hydrogen, $C_{1-6}$alkyl, $C_{1-6}$alkyloxy, halo, hydroxy, cyano, nitro, amino, mono- and di($C_{1-6}$alkyl)amino, aminocarbonyl, arylcarbonylamino, $C_{1-6}$alkylcarbonylamino, $C_{1-6}$alkylcarbonyl, $C_{1-6}$alkylcarbonyloxy, aminosulfonyl, $C_{1-6}$alkylsufinyl, $C_{1-6}$alkylsulfonyl, $C_{1-6}$alkylthio, mercapto, $C_{3-6}$alkynyloxy, $C_{3-6}$alkenyloxy, aryl$C_{1-6}$alkyloxy, aryloxy and $C_{1-6}$alkyl substituted with up to 4 halo atoms;

Alk is $-CH_2-CH_2-$ or $-CH_2-CH(CH_3)-$;

$Ar^1$ and $Ar^2$ are, each independently, phenyl or halophenyl;

$R^6$ and $R^7$ are, each independently, hydrogen, $C_{1-6}$alkyl, phenylmethyl methyl or 2-propenyl or $R^6$ and $R^7$ combined with the nitrogen atom bearing said $R^6$ and $R^7$ may form a pyrrolidinyl, piperidinyl, $C_{1-6}$alkylpiperidinyl, 4-morpholinyl or 2,6-di($C_{1-6}$alkyl)-4-morpholinyl radical;

wherein aryl is a member selected from the group consisting of phenyl being optionally substituted with up to 3 substituents. i.e. 1, 2 or 3, each independently selected from the group consisting of halo, hydroxy, $C_{1-6}$alkyl, $C_{1-6}$alkyloxy, aminosulfonyl, $C_{1-6}$alkylcarbonyl, nitro, trifluoromethyl, amino, aminocarbonyl and phenylcarbonyl, said phenylcarbonyl being optionally substituted with up to 3 halo atoms; and thienyl being optionally substituted with halo or $C_{1-6}$alkyl.

As used in the foregoing definitions the term halo is generic to fluoro, chloro, bromo and iodo; "$C_{1-6}$alkyl" is meant to include straight and branched saturated hydrocarbon radicals, having from 1 to 6 carbon atoms, such as, for example, methyl, ethyl, 1-methylethyl, 1,1-dimethylethyl, propyl, butyl, pentyl, hexyl and the like. "$C_{3-6}$alkenyl" is meant to include straight and branch chained hydrocarbon radicals containing one double bond and having from 3 to 6 carbon atoms such as, for example 3-propenyl. 2-butenyl and the like; "$C_{3-6}$alkynyl" is meant to include straight and branch chained hydrocarbon radicals having one triple bond and having from 3 to 6 carbon atoms such as, for example, propargyl, 2-butynyl, 3-butynyl, 2-pentynyl and the like.

The said N-oxides of the compounds of formula (I) are meant to comprise those compounds of formula (I) wherein one or several nitrogen atoms are oxidated to the so called N-oxide form. Particularly those N-oxides wherein the piperidine-nitrogen is N-oxidated. The present invention is particularly concerned with a method of treating warm-blooded animals suffering from diarrhea, which method comprises the systemic administration to warm-blooded animals of an amount effective in treating diarrhea of a compound of formula (I) wherein the substituents in the 3- and 4-position of the piperidine ring have the trans configuration.

A number of active ingredients of formula (I) are novel and have especially been developed to be used as active substances in the method of the present invention. These compounds constituting a further aspect of the present invention can be represented by the formula

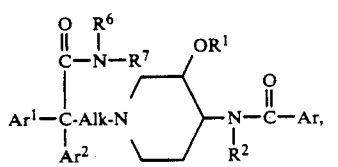

(I')

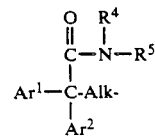

(II)

the N-oxide forms, pharmaceutically acceptable acid-addition salts and stereochemically isomeric forms thereof, wherein $R^1$, $R^2$, $R^6$, $R^7$, Ar, $Ar^1$, $Ar^2$ and Alk have the previously described meaning provided that Ar is other than phenyl or 4-amino-5-chloro-2-methoxyphenyl when $R^6$ and $R^7$ are both methyl.

Preferred novel compounds are those compounds of formula (I') wherein Ar is thienyl, halothienyl, furanyl, halofuranyl, pyridinyl, aminopyridinyl, thiazolyl, imidazolyl or a radical of formula

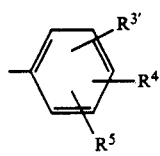

(a-2)

wherein $R^{3'}$ is $C_{3-6}$alkenyloxy, $C_{3-6}$alkynyloxy, aryl$C_{1-6}$alkyloxy, aryloxy or $C_{1-6}$alkyl substituted with up to 4 halo atoms, said $R^{3'}$ being substituted on either the ortho, para or meta position, and $R^4$ and $R^5$ have the previously described meanings.

More preferred novel compounds are those preferred novel compounds wherein the substituents in the 3- and 4-position of the piperidine ring have the trans configuration.

Particularly preferred novel compounds are those more preferred novel compounds having one or more of the following particular substituents: Ar is thienyl, halothienyl, furanyl, halofuranyl, pyridinyl, aminopyridinyl, thiazolyl, imidazolyl or a radical of formula (a-2) wherein $R^{3'}$ is phenylmethoxy, phenoxy, propenyloxy or $C_{1-4}$alkyl substituted with up to 4 halo atoms and $R^4$ and $R^5$ are each independently hydrogen, $C_{1-4}$alkyl, $C_{1-4}$alkyloxy, halo, hydroxy, nitro, amino, $C_{1-4}$alkyl substituted with up to 4 halo atoms, phenylmethoxy, phenoxy or propenyloxy; $R^1$ is hydrogen or $C_{1-4}$alkyl; or $R^6$ and $R^7$ are, each independently hydrogen, $C_{1-4}$alkyl, phenylmethyl or 2-propenyl, or $R^6$ and $R^7$ combined with the nitrogen bearing said $R^6$ and $R^7$ may form a pyrrolidinyl, piperidinyl or 4-morpholinyl radical.

Especially preferred novel compounds are those particularly preferred novel compounds wherein Ar is a radical of formula (a-2) wherein $R^{3'}$ is trifluoromethyl substituted on the meta position and $R^4$ and $R^5$ are each independently hydrogen, methyl, methoxy, halo, hydroxy, nitro, amino, trifluoromethyl, phenylmethoxy, phenoxy or propenyloxy.

The most preferred novel compounds within the invention are selected from the group consisting of trans-3-hydroxy-N,N,γ-trimethyl-α,α-diphenyl-4-[[3-(trifluoromethyl)benzoyl]amino]-1-piperidinebutanamide and the pharmaceutically acceptable acid-addition salts thereof.

In order to simplify the structural representations of the compounds of formula (I) and of certain precursors and intermediates thereof the -radical will hereafter be represented by the symbol L.

The compounds of formula (I) can generally be prepared by the amidation reaction of an amine of formula with a carboxylic acid of formula

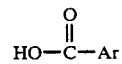

(III)

or a functional derivative thereof, such as, a halide, a symmetrical, a mixed or intramolecular anhydride, e.g. a cyclic anhydride of formula (III-a), or an activated ester, the latter also comprising internally activated esters such as, for example, the ester of formula (III-b).

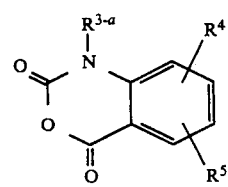

(III-a)

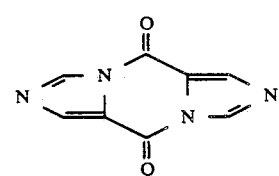

(III-b)

$R^{3-a}$ in formula (III-a) is hydrogen or mono$C_{1-6}$alkyl and $R^4$ and $R^5$ are as previously defined. Said functional derivatives may be generated in situ, or, if desired be isolated and further purified before reacting them with the amine of formula (II). Functional derivatives may be prepared following art-known methods, for example, by reacting the carboxylic acid of formula (III) with thionyl chloride, phosphorous trichloride, polyphosphoric acid, phosphoryl chloride and the like, or by reacting the carboxylic acid of formula (III) with an acid halide e.g. acetyl chloride, ethyl carbonochloridate and the like. Or, the compounds of formula (I) may be prepared by reacting (II) and (III) with a suitable reagent capable of forming amides, e.g., dicyclohexylcarbodiimide, 2-chloro-1-methylpyridinium iodide and the like. Said amidation reactions may conveniently be carried out by stirring a suitable reaction inert solvent such as, for example, a halogenated hydrocarbon, e.g. dichloromethane, trichloromethane and the like, an aromatic hydrocarbon, e.g. methylbenzene and the like, an ether, e.g. 1,1'-oxybisethane, tetrahydrofuran and the like or a polar aprotic solvent, e.g. N,N-dimethylformamide, N,N-dimethylacetamide and the like. The addition of a suitable base such as. N,N-diethylethanamine may be appropriate. The water, the alcohol or the acid which is liberated during the course of the reaction is preferably removed from the reaction mixture following art-known procedures such as, for example, by azeotropical distillation, by complexation, by salt formation and the like methods.

The compounds of formula (I) wherein $R^1$ is hydrogen and wherein the substituents in the 3- and 4-positions of the piperidine ring have the trans configuration, said compounds being represented by the formula (I-a-1), can also be prepared by reacting a 7-oxa-3-azabicyclo[4.1.0]-heptane of formula (IV) with an amide of formula (V). The compounds of formula (I-a-1) can further be O-alkylated or O-acylated following art-known procedures thus preparing the corresponding compounds of formula (I-a-2) wherein the substituents in the 3- and 4-positions of the piperidine ring have the trans configuration and wherein $R^1$ is other than hydrogen, said $R^1$ being represented by $R^{1-a}$.

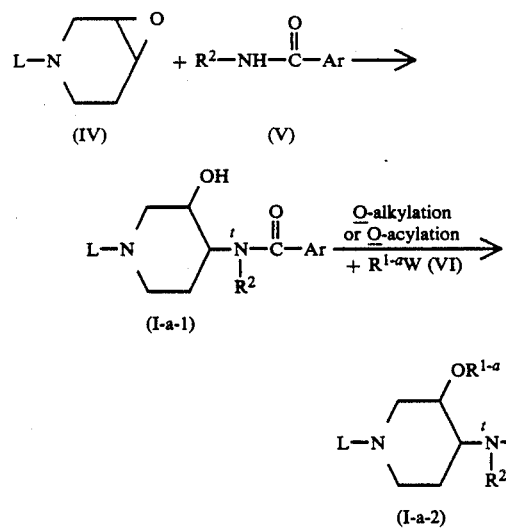

In (I-a-1) and (I-a-2) the symbol "t" indicates that the substituents are in trans configuration. In (VI) W represents an appropriate reactive leaving group such as, for example, halo, e.g. chloro, bromo or iodo, or a sulfonyloxy group, e.g. methylsulfonyloxy or (4-methylphenyl)sulfonyloxy.

The reaction of (IV) with (V) may conveniently be conducted by stirring and, if desired. heating the reactants in a suitable reaction-inert solvent, such as, for example, an alcohol, e.g., methanol, ethanol and the like.

The O-alkylation or O-acylation reactions are conveniently conducted in an inert organic solvent such as, for example, an aromatic hydrocarbon, e.g., benzene, methylbenzene, dimethylbenzene, and the like; a lower alkanol, e.g., methanol, ethanol, 1-butanol and the like; a ketone, e.g., 2-propanone, 4-methyl-2-pentanone and the like; an ether, e.g., 1,4-dioxane, 1,1'-oxybisethane, tetrahydrofuran and the like; or a dipolar aprotic solvent e.g. N,N-dimethylformamide (DMF), N,N-dimethylacetamide (DMA), dimethyl sulfoxide (DMSO), 1-methyl-2-pyrrolidinone, and the like. An appropriate base such as, for example, an alkali metal carbonate, sodium hydride or an organic base such as, for example, N,N-diethylethanamine or N-(1-methylethyl)-2-propanamine may be utilized to pick up the acid which is liberated during the course of the reaction. In some instances the addition of a iodide salt, preferably an alkali metal iodide, is appropriate. Somewhat elevated temperatures may enhance the rate of the reaction.

The compounds of formula (I) wherein the substituents in the 3- and 4-positions of the piperidine ring have the cis configuration, said compounds being represented by the formula (1-b), can also be prepared by the reductive N-alkylation of a piperidone of formula (VII) with an amide of formula (V).

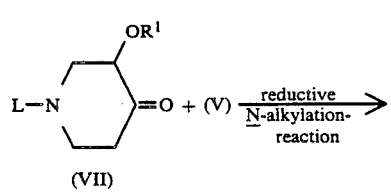

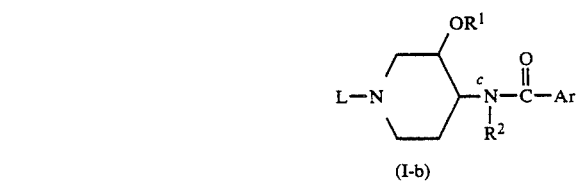

In (1-b) the symbol "c" indicates that the substituents are in cis configuration. Said reductive N-alkylation reaction may conveniently be carried out by catalytically hydrogenating a stirred and heated mixture of the reactants in a suitable reaction-inert organic solvent according to art-known catalytic hydrogenating procedures. Suitable solvents are, for example, water; alkanols, e.g. methanol, ethanol, 2-propanol and the like; cyclic ethers, e.g., 1,4-dioxane and the like; halogenated hydrocarbons, e.g. trichloromethane and the like; a polar aprotic solvent e.g. N,N-dimethylformamide, dimetbyl sulfoxide and the like; or a mixture of 2 or more of such solvents. The term "art-known catalytic hydrogenating procedures" means that the reaction is carried out under hydrogen atmosphere and in the presence of an appropriate catalyst such as, for example, palladium-on-charcoal, platinum-on-charcoal and the lke. In order to prevent the undesired further hydrogenation of certain functional groups in the reactants and the reaction products it may be advantageous to add an appropriate catalyst-poison to the reaction mixture, e.g., thiophene and the like.

The compounds of formula (I), can also be prepared by N-alkylating a piperidine of formula (VIII) with an intermediate of formula (IX) or with an ammonium salt of formula (X).

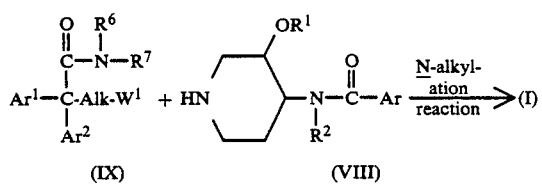

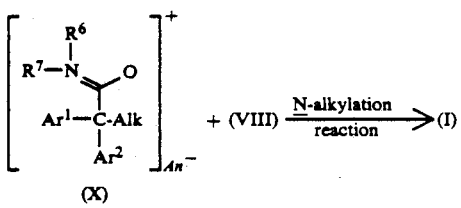

In (IX) $W^1$ represents an appropriate leaving group such as, for example, halo, e.g. chloro, bromo or iodo, or a sulfonyloxy group, e.g. methylsulfonyloxy or 4-methylsulfonyloxy. In (X) $An^-$ represents an appropriate anion such as, for example, a halide anion, e.g. chloride, bromide or iodide. Said N-alkylation reactions are conveniently conducted in an inert organic solvent such as, for example, an aromatic hydrocarbon. e.g., benzene, methylbenzene, dimethylbenzene, and the like; an alkanol, e.g., methanol, ethanol, 1-butanol and the like; a ketone, e.g., 2-propanone, 4-methyl-2-pentanone and the like; an ether, e.g., 1,4-dioxane, 1,1'-oxybisethane, tetrahydrofuran and the like; a dipolar aprotic solvent e.g. N,N-dimethylformamide (DMF), N,N-dimethylacetamide (DMA), nitrobenzene, dimethyl sulfoxide (DMSO), 1-methyl-2-pyrrolidinone, and the like. The addition of an appropriate base such as, for example, an alkali metal carbonate or hydrogen carbonate or an organic base such as, for example, N,N-diethylethanamine or N-(1-methylethyl)-2-propanamine may be suited to pick up the acid Which is liberated during the course of the reaction. In some instances the addition of a iodide salt, preferably an alkali metal iodide, is appropriate. Somewhat elevated temperatures may enhance the rate of the reaction.

The compounds of formula (I) can alternatively be prepared by the reductive amination reaction of an appropriate ketone or aldehyde of formula $L'=O$ (XI), said $L'=O$ being a compound of formula L-H wherein two geminal hydrogen atoms are replaced by $=O$, with a piperidine of formula (VIII).

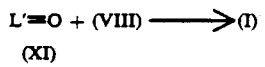

The compounds of formula (I) can also be converted into each other following art-known procedures of functional group transformation. Some examples thereof will be cited hereinafter.

The compounds of formula (I) having a nItro substituent can be converted into the corresponding amines by stirring and, if desired, heating the starting nitro-compounds in a hydrogen-containing medium in the presence of a suitable amount of an appropriate catalyst such as, for example, platinum-on-charcoal, palladium-on-charcoal, Raney-nickel and the like catalysts. Suitable solvents are, for example, methanol, ethanol and the like.

The hydrogen atom of the amino function of compounds of formula (I) may be replaced following art-known procedures such as, for example, N-alkylation, reductive N-alkylation, N-acylation and the like methods:

(1) alkylcarbonyl, arylcarbonyl and the like groups may be introduced by reacting the starting amine with an appropriate carboxylic acid or a derivative thereof such as. for example, an acid halide, acid anhydride and the like.

(2) alkyl groups may be introduced by reacting the starting amine with an alkanal or alkanone under a hydrogen atmosphere and in the presence of an appropriate catalyst such as, palladium-on-charcoal, platinum-on-charcoal and other like catalysts in suitable solvent such as, methanol, ethanol and the like. In order to prevent the undesired further hydrogenation of certain functional groups in the reactants and the reaction products it may be advantageous to add an appropriate catalyst-poison to the reaction mixture, e.g., thiophene and the like.

Compounds of formula (I) containing a hydroxy function may be converted into compounds of formula (I) containing a $C_{1-6}$alkylcarbonyloxy function by stirring the former with an appropriate acylating agent, e.g. an acid anhydride.

The compounds of formula (I) wherein Ar is phenyl substituted with phenylmethoxy may be converted into compounds of formula (I) wherein Ar is phenyl substituted with hydroxy following art-known catalytic hydrogenolysis procedures.

Halo atoms substituted on the benzamide moiety may be replaced by hydrogen following art-known hydrogenolysis procedures, i.e. by stirring and, if desired, heating the starting compounds in a suitable solvent under hydrogen atmosphere in the presence of an appropriate catalyst, e.g. palladium-on-charcoal and the like catalysts.

The compounds of formula (I) can be converted to the corresponding N-oxide forms following art-known procedures for converting a trivalent nitrogen to its N-oxide-form. Said N-oxidation reaction may generally be carried out by reacting the starting material of formula (I) with an appropriate organic or inorganic peroxide. Appropriate inorganic peroxides comprise, for example, hydrogen peroxide, an alkali metal or earth alkaline metal peroxide, e.g. sodium peroxide, potassium peroxide, barium peroxide and the like; appropriate organic peroxides may comprise peroxy acids such as, for example, benzenecarboperoxoic acid or halo substituted benzenecarboperoxoic acid, e.g. 3-chlorobenzenecarboperoxoic acid and the like, peroxoalkanoic acids, e.g. peroxoacetic acid and the like, alkylhydroperoxides, e.g. t.butyl hydroperoxide and the like. If desired, said N-oxidation may be carried out in a suitable solvent such as for example, water, lower alkanols, e.g. methanol, ethanol, propanol, butanol and the like, hydrocarbons, e.g. benzene, methylbenzene, dimethylbenzene and the like, ketones, e.g. 2-propanone, 2-butanone and the like, halogenated hydrocarbons, e.g. dichloromethane, trichloromethane and the like, and mixtures of such solvents. In order to enhance the reaction rate. it may be appropriate to heat the reaction mixture.

In all of the foregoing and in the following preparations, the reaction products may be isolated from the reaction mixture and. if necessary. further purified according to methodologies generally known in the art.

The compounds of formula (I) having basic properties may be converted to their therapeutically active non-toxic acid addition salt forms by treatment with appropriate acids, such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

Conversely the salt form can be converted by treatment with alkali into the free base form.

Some of the intermediates and starting materials in the foregoing preparations are known compounds while others are novel. They may be prepared according to art-known methodologies of preparing said known or similarly known compounds. Some procedures for preparing such intermediates will be described hereinafter in more detail.

The intermediates of formula (II) can be derived from an appropriately substituted piperidine of formula (XII) by reacting the latter with a reagent of formula (IX) or (X), following the N-alkylation procedures described for the preparation of (I) starting from (X) and (VIII) and, subsequently, eliminating the protective group P in the thus obtained intermediate following art-known procedures, e.g., depending upon the case by hydrolysis in acidic or alkaline aqueous medium or by catalytic hydrogenation.

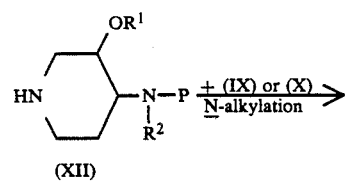

(XII)

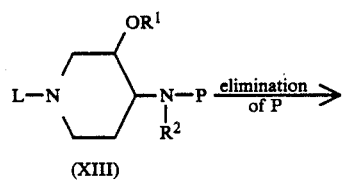

(XIII)

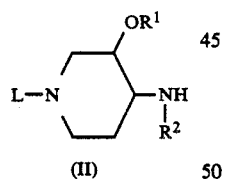

(II)

The intermediates of formula (VIII) can be derived from an appropriately substituted piperidine formula of (XIV) by reacting the latter with a reagent of formula (III) or a functional derivative thereof, following the amidation procedures described for the preparation of (I) starting from (II) and (III), and subsequently eliminating the protective group P in the thus obtained intermediate following art-known procedures.

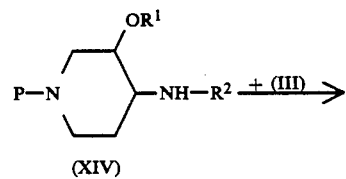

(XIV)

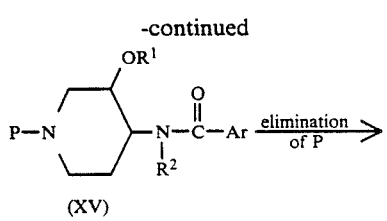

(XV)

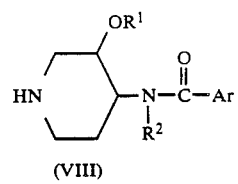

(VIII)

In the foregoing and following reaction schemes P represents a suitable protective group which is readily removable by hydrogenation or hydrolysation, such as, phenylmethyl, $C_{1-4}$alkyloxycarbonyl and the like groups.

In general, the piperidines (XII), (XIV), (VII) and (IV) used as starting materials, can be prepared following procedures analogous to those described in the published Eur. Pat. Appl. No. 0,076,530 which corresponds to U.S. application Ser. No. 362,814, and in Drug Development Research 8, 225–232 (1986).

The piperidines (XIV) wherein the substituents in the 3- and 4-position of the piperidine ring have the trans configuration, said piperidines being represented by formula (XIV-a), are preferably prepared from an appropriately substituted 7-oxa-3-azabicyclo[4.1.0]heptane, (XVI), by reacting the latter with an alkali metal azide (XVII) in a suitable reaction inert medium and by hydrogenating the thus obtained 4-azide-3-hydroxypiperidine, (XVIII), in the presence of a nobel catalyst, optionally after O-alkylating or O-acylating the hydroxy substituent with a reagent of formula (VI) following procedures described hereinabove for the preparation of (1-a-2) starting from (I-a-1) and (VI).

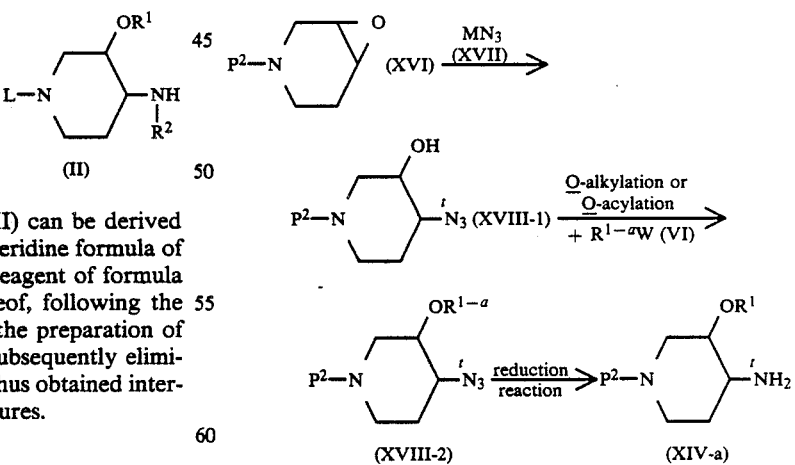

In formula (XVII) M is an appropriate alkali metal ion such as, for example, natrium, kalium and the like ions.

The compounds of formula (XIV). can easily be converted into the compounds of formula (XII) by introducing a protective group $P^1$ on the primary amine function, and selectively eliminating the protective group $P^2$ on the secondary amine function.

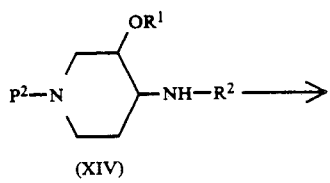

(XIV)

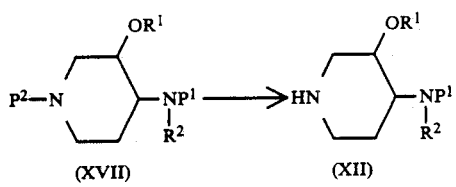

(XVII) (XII)

The protective groups $P^1$ and $P^2$ should be selected so that $P^2$ can be eliminated without affecting $P^1$. Suitable protective groups are, for example, hydrogenolyzable groups as $P^1$ radicals, e.g. a phenylmethyl group and the like, and hydrolyzable groups as $P^2$ radicals, e.g., a $C_{1-6}$alkylcarbonyl group and the like.

The intermediates of formula (IX) and (X) and their preparations are described in U.S. Pat. No. 3,714,159 and in the Journal of Medicinal Chemistry, 16,782 (1973). All references mentioned hereinabove are incorporated herein by reference.

The intermediates of formula (VIII) wherein Ar is thienyl, halothienyl, furanyl, halofuranyl, pyridinyl, aminopyridinyl, thiazolyl, imidazolyl or a radical of formula

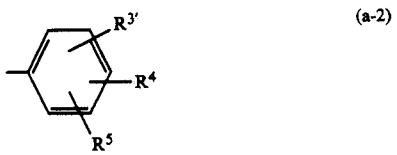

(a-2)

wherein $R^{3'}$ is aryl$C_{1-6}$alkyloxy, aryloxy, $C_{3-6}$alkenyloxy, $C_{3-6}$alkynyloxy or $C_{1-6}$alkyl substituted with up to 4 halo atoms and $R^4$ and $R^5$ have the previously described meanings, said intermediates being represented by (VIII-a) are deemed to be novel intermediates, and as such they represent an additional feature of the present invention. The compounds of formula (I) and some of the intermediates in this invention have one or more asymmetric carbon atom in their structure. Each of the chiral centers may be present in a R- or S-configuration, this R- and s-notation being In correspondence with the rules described in J. Org. Chem., 35, 2849–2867 (1970).

Pure stereochemically isomeric forms of the compounds of formula (I) may be obtained by the application of art-known procedures. Diastereoisomers may be separated by physical separation methods such as selective crystallization and chromatographic techniques, e.g., counter current distribution, and enantiomers may be separated from each other by the selective crystallization of their diastereomeric salts with optically active acids.

Pure stereochemically isomeric forms may also be derived from the corresponding pure stereochemically isomeric forms of the appropriate starting materials, provided that the reaction occurs stereospecifically.

It is evident that the cis and trans diastereomeric racemates may be further resolved into their optical isomers, cis(+), cis(−), trans(+) and trans(-) by the application of methodologies known to those skilled in the art.

In some compounds the stereochemical configuration is not experimentally determined. In those cases it is conventionally agreed to designate tbe stereochemically isomeric form which is first isolated as "A" or "X" and the second as "B" or "Y", without further reference to the actual stereochemical configuration.

Stereochemically isomeric forms of the compounds of formula (I) are naturally intended to be embraced within the scope of the invention.

The use of the compounds of formula (I), their N-oxide forms, pharmaceutically acceptable acid-addition salts and stereoisomeric forms thereof in the method of the present invention is based on their useful antidiarrheal activity. This property is clearly evidenced by the experimental data obtained in, for example, the "Ricinus oil Test in Rats". The subject compounds are particularly attractive due to the strongly decreased and often absent undesired central effects. This can be demonstrated by the results of, for example, the "Tail Withdrawal Test in Rats". By virtue of their useful antidiarrheal activity, it is evident that the compounds of formula (I), their N-oxide forms, pharmaceutically acceptable acid addition salts and stereoisomeric forms can be used in the treatment of diarrhea. Due to the strongly decreased and often absent undesired central effects, they can particularly be useful in the treatment of diarrhea in subjects where medicines having undesired central effects can be harmful, for example, in the treatment of children and infants.

In view of their useful antidiarrheal properties, the subject compounds may be formulated into various Pharmaceutical forms for administration purposes.

To prepare the pharmaceutical compositions of this invention, an effective amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those of skill in treating diarrhea could easily determine the effective amount from the test results presented hereinafter. In general it is contemplated that an effective amount would be from 0.001 mg/kg to 10 mg/kg body weight, more preferably from 0.005 mg/kg to 5 mg/kg body weight.

The following examples are intended to illustrate and not to limit the scope of the present invention in all its aspects. Unless otherwise stated all parts therein are by weight.

EXPERIMENTAL PART

A. Preparation of Intermediates

EXAMPLE 1

(a) Gazeous carbonic dichloride was bubbled through a stirred solution of 16.1 parts of 2-amino-6-methoxybenzoic acid in 16.8 parts of concentrated hydrochloric acid and 140 parts of water for 2 hours. Gazeous nitrogen was bubbled through this mixture for 15 minutes. The product was filtered off, washed with water and dried, yielding 16.5 parts (88.9%) of 5-methoxy-2H-3,1-benzoxazine-2,4(1H)-dione (interm. 1).

(b) To a stirred and cooled (<10° C.) solution of 9.65 parts of 5-methoxy-2H-3,1-benzoxazine-2,4(1H)-dione in 54 parts of N,N-dimethylformamide were added portionwise 2.64 parts of a sodium hydride dispersion 50%. After stirring for 1 hour in an ice bath. 7.81 parts of iodomethane were added dropwise at <15° C. When the reaction mixture was solidified, 45 parts of N,N-dimethylformamide were added and a sodium hydride dispersion 50% was further added dropwise. Upon complete addition, stirring was continued overnight while the reaction mixture was allowed to reach room temperature. The reaction mixture was poured into ice water and 2,2'-oxybispropane was added. The precipitated product was filtered off, washed with water and dried, yielding 8.37 parts (80.7%) of 5-methoxy-1-methyl-2H-3,1-benzoxazine-2,4(1H)-dione; mp. 215.8° C. (interm. 2)

EXAMPLE 2

(a) To a stirred emulsion of 53.8 parts of ethyl 7-oxa-3-azabicyclo-[4.1,0]heptane-3-carboxylate, 17.6 parts of ethanol and 195 parts of water were added portionwise, during a 15 minutes-period, 28.6 parts of sodium azide while cooling in an ice bath. The mixture was warmed slowly to room temperature and stirring was continued overnight at room temperature. The aqueous phase was separated and extracted twice with dichloromethane. The combined organic phases were washed with a small amount of water, dried, filtered and evaporated, yielding 56.3 parts (82%) of a mixture of 80% of ethyl trans-4-azido-3-hydroxy-1-piperidinecarboxylate (interm. 3) and 15% of ethyl trans-3-azido-4-hydroxy-1-piperidinecarboxylate.

(b) To a stirred solution of 20.6 parts of 2-methyl-2-propanol, potassium salt in 54 parts of N,N-dimethylformamide was added dropwise a solution of 30.3 parts of a mixture of ethyl trans-4-azido-3-hydroxy-1-piperidinecarboxylate and ethyl trans-3-azido-4-hydroxy-1-piperidinecarboxylate in 45 parts of N,N-dimethylformamide at a temperature below 20° C. (ice bath). Upon completion, stirring was continued for 1 hour at room temperature. 25.9 parts of iodomethane were added dropwise at a temperature <10° C. Upon completion, stirring was continued overnight at room temperature. The reaction mixture was poured into 400 parts of water. The product was extracted with trichloromethane. The extract was washed with a sodium chloride solution, dried, filtered and evaporated in vacuo. The residue was purified by column chromatography over silica gel using trichloromethane as eluent. The desired fractions were collected and the eluent was evaporated, yielding 15.6 parts (48.8%) of ethyl trans-4-azido-3-methoxy-1-piperidinecarboxylate as a residue (interm. 4).

(c) A mixture of 15.6 parts of ethyl trans-4-azido-3-methoxy-1-piperidinecarboxylate and 200 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated in vacuo, yielding 13.8 parts (97.4%) of ethyl trans-4-amino-3-methoxy-1-piperidinecarboxylate as a residue (interm. 5).

EXAMPLE 3

(a-1) A mixture of 51.3 parts of ethyl 7-oxa-3-azabicyclo[4.1.0]heptane-3-carboxylate. 36.4 parts of N-methylbenzenemethanamine and 480 parts of ethanol was stirred and refluxed for 42 hours. The reaction mixture was evaporated and the residue was taken up in a dilute hydrochloric acid solution. The aqueous phase was washed three times with 2,2'-oxybispropane and alkalized with a sodium hydroxide solution 50%. The product was extracted with dichloromethane. The extract was washed with water, dried, filtered and evaporated. The residue was purified by column chromatography over silica gel using a mixture of trichloromethane and methanol (97:3 by volume) as eluent. The pure fractions were collected and the eluent was evaporated, yielding 45 9 parts (52.3%) of a mixture of ethyl trans-4-hydroxy-3-[methyl(phenylmethyl)amino-]1-piperidinecarboxylate and ethyl trans-3-hydroxy-4-[methyl(phenylmethyl)amino]-1-piperidinecarboxylate (interm. 6) in the proportion of 62.3% and 32.9%. Intermediate 6 was also prepared according to the following procedure:

(a-2) A mixture of 40 parts of ethyl trans-3-hydroxy-4-[(phenylmethyl)-amino]-1-piperidinecarboxylate, 15 parts of poly(oxymethylene), 2 parts of a solution of thiophene in methanol and 400 parts of methanol was hydrogenated at normal pressure and at room temperature with 4 parts of palladium-on-charcoal catalyst 10%. After the calculated amount of hydrogen was taken up, the catalyst was filtered off and the filtrate was evaporated. The residue was dissolved in trichloromethane. The organic layer was washed successively with a dilute ammonium hydroxide solution and water, dried, filtered and evaporated in vacuo. The residue was crystallized from 80 parts of acetonitrile The product was filtered off and dried, yielding 32.7 parts (79.9%) of ethyl trans-3-hydroxy-4-[methyl(phenylmethyl)amino]-1-piperidinecarboxylate (interm. 6).

(b) A mixture of 45.9 parts of ethyl trans-4-hydroxy-3-[methyl(phenylmethyl)amino]-1-piperidinecarboxylate and ethyl trans-3-hydroxy-4-[methyl(phenylmethyl)amino]-1-piperidinecarboxylate, 87.9 parts of potassium hydroxide and 576 parts of 2-propanol was stirred and refluxed for 4 hours. The reaction mixture was evaporated, water was added and evaporation was continued till all traces of 2-propanol were removed. The product was extracted three times with dichloromethane. The combined extracts were washed with a small amount of water, dried, filtered and evaporated. The residue was purified by column chromatography over silica gel using a mixture of trichloromethane and methanol, saturated with ammonia, (92:8 by volume) as eluent. The pure fractions were collected and the eluent was evaporated, yielding 32 parts of a mixture of trans-3-[methyl(phenylmethyl)amino]-4-piperidinol and trans-4-[methyl(phenylmethyl)amino]-3-piperidinol (Interm. 7).

EXAMPLE 4

(a) To a stirred solution of 10 parts of trans-3-methoxy-1-(phenylmethyl)-4-piperidinamine and 5.95 parts of N,N-diethylethanamine in 75 parts of trichloromethane was added dropwise a solution of 10.4 parts of 3-(trifluoromethyl)benzoyl chloride in 15 parts of N,N-diethylethanamine while cooling in an ice bath. Upon completion, stirring was continued for 20 hours at room temperature. The mixture was washed twice with a sodium hydroxide solution 5% and once with water and then dried, filtered and evaporated in vacuo. After crystallization of the residue from 27 parts of methylbenzene, the product was filtered off, washed with 45 parts of methylbenzene and dried, yielding 14.4 parts (80.9%) of trans-N-[3-methoxy-1-(phenylmethyl)-4-piperidinyl]-3-(trifluoromethyl)benzamide; mp. 135.2° C. (interm. 8).

A mixture of 12 parts of trans-N-[3-methoxy-1-(phenylmethyl)-4-piperidinyl]-3-(trifluoromethyl)benzamide and 200 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated in vacuo. The residue was solidified on scratching in 2,2'-oxybispropane. The precipitated product was filtered off and dissolved in 135 parts of methylbenzene and 105 parts of 1,1'-oxybisethane. The supernatant liquid was decanted, washed twice with a dilute ammonium hydroxide solution and the product was extracted with methylbenzene. The aqueous phase was saturated with potassium carbonate and the product was extracted with methylbenzene. The combined organic layers were dried, filtered and evaporated in vacuo, yielding 6.43 parts (71%) of trans-N-(3-methoxy-4-piperidinyl)-3-(trifluoromethyl)benzamide; mp. 100.3° C. (interm. 9).

In a similar manner there were also prepared:
cis-N-(3-methoxy-4-piperidinyl)-2-phenoxybenzamide; mp. 93.9° C. (interm. 10);
cis-5-chloro-N-(3-methoxy-4-piperidinyl)-2-phenoxybenzamide ethanedioate (1:1); mp. 180.9° C. (interm. 11); and
trans-N-(3-hydroxy-4-piperidinyl)-3-(trifluoromethyl)benzamide; mp 164.8° C. (interm. 12).

EXAMPLE 5

(a) To a stirred and cooled (5° C.) suspension of 81 parts of 4-chloro-2-methoxy-5-nitrobenzoic acid in 1350 parts of trichloromethane were added first 35.4 parts of N,N-diethylethanamine and then 38 parts of ethyl carbonochloridate at a temperature below 5° C. The whole was stirred for 2 hours in an ice bath. A solution of 65 parts of ethyl cis-4-amino-3-methoxy-1-piperidinecarboxylate in 1125 parts of trichloromethane was added while the temperature was kept below 10° C. Stirring was continued first for 1 hour in an ice bath and then overnight at room temperature. The mixture was washed successively once with water, twice with a sodium hydroxide solution 5% and three times with water, dried, filtered and evaporated. The residue was crystallized from acetonitrile. The product was filtered off and dried, yielding 100 parts (75%) of ethyl cis-4-[(4-chloro-2-methoxy-5-nitro-benzoyl)amino]-3-methoxy-1-piperidinecarboxylate; mp. 181.3° C. (interm. 13).

(b) A mixture of 90.5 parts of ethyl cis-4-[(4-chloro-2-methoxy-5-nitrobenzoyl)amino]-3-methoxy-1-piperidinecarboxylate, 3 parts of a solution of thiophene in methanol 4% and 400 parts of methanol was hydrogenated at normal pressure and at 50° C. with 5 parts of platinum-on-charcoal catalyst 5%. After the calculated amount of hydrogen was taken up, the catalyst was filtered off and the filtrate was evaporated. The residue was crystallized from 2-propanol. The product was filtered off and dried, yielding 80 parts (94%) of ethyl cis-4-[(5-amino-4-chloro-2-methoxybenzoyl)amino]-3-methoxy-1-piperidinecarboxylate: mp. 142.5° C. (interm. 14).

(c) A mixture of 81 parts of ethyl cis-4-[(5-amino-4-chloro-2-methoxybenzoyl)amino]-3-methoxy-1-piperidinecarboxylate, 122 parts of potassium hydroxide and 800 parts of 2-propanol was stirred for 6 hours at reflux temperature. The whole was stirred overnight at room temperature. The reaction mixture was evaporated. The residue was taken up in water and heated for a while. The mixture was evaporated again. The residue was taken up in water and the aqueous phase was extracted twice with dichloromethane. The combined organic layers were washed with water, dried, filtered and evaporated. The residue was crystallized from acetonitrile. The product was filtered off and dried, yielding 58 parts (85%) of cis-5-amino-4-chloro-2-methoxy-N-(3-methoxy-4-piperidinyl)benzamide; mp. 191.8° C. (interm. 15).

In a similar manner there were also prepared:
trans-4-amino-5-chloro-N-(3-hydroxy-4-piperidinyl)-2-methoxybenzamide; mp. 185.2° C. (interm. 16); and
trans-4-amino-5-chloro-2-methoxy-N-(3-methoxy-4-piperidinyl)benzamide mp. 136.3° C. (interm. 17).

EXAMPLE 6

(a) A mixture of 17.6 parts of trans-4-[(phenylmethyl)amino]-3-piperidinol, 27 parts of sodium carbonate and 680 parts of 4-methyl-2-pentanone was stirred and refluxed for 45 minutes using a water separator. After cooling, 33.8 parts of N-(dihydro-5-methyl-3,3-diphenyl-2(3H)-furanylidene)-N-methylmethanaminium bromide were added and stirring was continued for 24 hours at reflux. The mixture was cooled and washed with water. The organic layer was dried, filtered and evaporated. The residue was dissolved in 1,1'-oxybisethane and acidified with 2-propanol, saturated with hydrogen chloride. The liquid was decanted and the half solid precipitated product was dissolved in water and treated with ammonium hydroxide. The product was extracted with trichloromethane. The extract was dried, filtered and evaporated. The residue was purified by column chromatography over silica gel using a mixture of trichloromethane and methanol, saturated with ammonia, (90:10 by volume) as eluent. The desired fractions were collected and the eluent was evaporated. The residue was solidified on scratching in petroleum ether. The product was filtered off and crystallized twice from acetonitrile. The product was filtered off and dried, yielding 18.8 parts (45%) of trans-3-hydroxy-N,N,$\gamma$-trimethyl-$\alpha$,$\alpha$-diphenyl-4-[(phenylmethyl)amino]-1-piperidinebutanamide; mp. 134.5° C. (interm. 18).

(b) A mixture of 63 parts of trans-3-hydroxy-N,N,$\gamma$-trimethyl-$\alpha$,$\alpha$-diphenyl-4-[(phenylmethyl)amino]-1-piperidinebutanamide and 485 parts of 2-methoxyethanol was hydrogenated at normal pressure and at 50° C. with 5 parts of palladium-on-charcoal catalyst 10%. After the calculated amount of hydrogen was taken up, the catalyst was filtered off and the filtrate was evaporated with methylbenzene, yielding 45 parts (87.5%) of trans-4-amino-3-hydroxy-N,N,$\gamma$-trimethyl-$\alpha$,$\alpha$-diphenyl-1-piperidinebutanamide (interm. 9).

In a similar manner there were also prepared:
trans-4-amino-3-hydroxy-N,N-dimethyl-$\alpha$,$\alpha$-diphenyl-1-piperidinebutanamide (interm. 20);
trans-3-hydroxy-,N,N,$\gamma$-trimethyl-4-(methylamino)-$\alpha$,$\alpha$-diphenyl-1-piperidinebutanamide; mp. 93.7° C. (interm. 21);
trans-1-[4-(4-amino-3-hydroxy-1-piperidinyl)-1-oxo-2,2-diphenylpentyl]-pyrrolidine as a residue (interm. 22);
trans-4-[4-(4-amino-3-hydroxy-1-piperidinyl)-1-oxo-2,2-diphenylpentyl]-morpholine as a residue (interm. 23); and
cis-4-amino-3-hydroxy-N,N,$\gamma$-trimethyl-$\alpha$,$\alpha$-diphenyl-1-piperidinebutanamide as a residue (interm. 24).

EXAMPLE 7

(a) A mixture of 29 parts of ethyl trans-4-amino-3-hydroxy-1-piperidinecarboxylate, 23.2 parts of (−)-[S-(R*,R*)]-2,3-dihydroxybutanedioc acid and 200 parts of ethanol was heated and the product was allowed to crystallize. After four crystallizations from ±320 parts of ethanol, the product was filtered off and dried, yielding 12 parts (21.3%) of (−)-ethyl (3B,trans)-4-amino-3-hydroxy-1-piperidinecarboxylate [S-(R*,R*)]-(2,3-dihydroxybutanedioate(1:1).monohydrate; mp. 148.8° C.; $[\alpha]_{365}^{25}$ = −40.03° (c=1% in water) (interm. 25).

(b) A mixture of 11 parts of (−)-ethyl (3B,trans)-4-amino-3-hydroxy-1-piperidinecarboxylate [S-(R*,R*)]-2,3-dihydrourybutanedioate (1:1), 4.2 parts of benzaldehyde, 2 parts of a solution of thiophene in methanol 4%, 7.4 parts of potassium acetate and 200 parts of methanol was hydrogenated at normal pressure and at room temperature with 3 parts of platinum-on-charcoal catalyst 5%. 3.6 Parts of potassium hydroxide were added and after the calculated amount of hydrogen was taken up, the catalyst was filtered off and the filtrate was evaporated. The residue was converted into the hydrochloride salt in 2-propanol. The salt was filtered off and dried, yielding 10 parts (97.7%) of (+)-ethyl (3B,trans)-3-hydroxy-4-[(phenylmethyl)amino]-1-piperidinecarboxylate monohydrochloride; mp. 159.8° C.; $[\alpha]_{365}^{25}$ = +78.46° (c=1% in ethanol) (interm. 26).

(c) A mixture of 8.5 parts of (+)-ethyl (3B,trans)-3-hydroxy-4-[(phenylmethyl)amino]-1-piperidinecarboxylate, 16.8 parts of potassium hydroxide and 120 parts of 2-propanol was stirred for 8 hours at reflux temperature. After evaporation, water was added to the residue and the solvent was evaporated again. The residue was taken up in water and the product was extracted with dichloromethane. The extract was washed with water, dried, filtered and evaporated. The residue was converted into the hydrochloride salt in 2-propanol and 2,2'-oxybispropane. The salt was filtered off and dried, yielding 1.35 parts (16.1%) of (+)-(3B,trans)-4-[(phenylmethyl)amino]-3-piperidinol dihydrochloride; mp. 196.6° C.; $[\alpha]_{365}^{25}$ = +92.01° (c=1% in ethanol) (interm. 27).

(d) A mixture of 8.8 parts of (+)-(3B,trans)-4-[(phenylmethyl)amino]-3-piperidinol, 6.3 parts of sodium carbonate and 200 parts of 4-methyl-2-pentanone was stirred and refluxed for 30 minutes using a water separator. After cooling, 16.9 parts of N-(dihydro-5-methyl-3,3-diphenyl-2(3H)-furanylidene)-N-methylmethanaminium bromide were added and stirring was continued for 17 hours at reflux. The mixture was filtered and the filtrate was evaporated. The residue was purified by column chromatography over silica gel using a mixture of trichloromethane and methanol, (95:5 by volume) as eluent. The pure fractions were collected and the eluent was evaporated. The residue was stirred in a mixture of acetonitrile and 2,2'-oxybispropane. The product was filtered off and dried, yielding 11.5 parts (55.0%) of (−)-(3B,trans)-3-hydroxy-N,N,$\gamma$-trimethyl-$\alpha$,$\alpha$-diphenyl-4-[(phenylmethyl)amino]-1-piperidinebutanamide (interm. 28).

(e) A mixture of 9.5 parts of (−)-(3B,trans)-3-hydroxy-N,N,$\gamma$-trimethyl-$\alpha$,$\alpha$-diphenyl-4-[(phenylmethyl)amino]-1-piperidinebutanamide and 200 parts of methanol was hydrogenated at normal pressure and at 50° C. with 2 parts of palladium-on-charcoal catalyst 10%. After the calculated amount of hydrogen was taken up, the catalyst was filtered off and the filtrate was evaporated, yielding 10 parts (100%) of (+)-(3B,trans)-4-amino-3-hydroxy-N,N,$\gamma$-trimethyl-$\alpha$,$\alpha$-diphenyl-1-piperidinebutanamide; $[\alpha]_{365}^{25}$ = +49.62° (c=1% in ethanol) (interm. 29).

In a similar manner there were also prepared:
(−)-(3A,trans)-4-amino-3-hydroxy-N,N,$\gamma$-trimethyl-$\alpha$,$\alpha$-diphenyl-1-piperidinebutanamide,
$[\alpha]_{589}^{25}$ = −13.68° (c=1% in ethanol) (interm. 30).

EXAMPLE 8

(a) A mixture of 20 parts of (+)-(3B,trans)-4-[(phenylmethyl)amino]-3-piperidinol, 14.3 parts of sodium carbonate and 454 parts of 4-methyl-2-piperidinol, pentanone was stirred and refluxed for 30 minutes using a water separator. After cooling, 38.4 parts of N-(dihydro-5-methyl-3,3-diphenyl-2(3H)-furanylidene)-N-methylmethanaminium bromide were added and stirring was continued for 18 hours at reflux. The mixture was filtered and the filtrate was evaporated. The residue was purified by column chromatography over silica gel using a mixture of trichloromethane and methanol (95:5 by volume) as eluent. The desired fractions were collected and the eluent was evaporated. The residue was stirred in a mixture of acetonitrile and 2,2'-oxybispropane. The precipitated product was filtered off and crystallized twice from acetonitrile. The product was filtered off and dried, yielding 11.4 parts (23.9%) of (−)-[1(Y),3B, trans]-3-hydroxy-N,N,γ-trimethyl-α,α-diphenyl-4-[(phenylmethyl)amino]-1-piperidinebutanamide, $[\alpha]_{589}^{25} = +6.60°$ (c=1% in ethanol) (interm. 31).

(b) A mixture of 11 parts of (−)-[1(Y),3B,trans]-3-hydroxy-N,N,γ-trimethyl-α,α-diphenyl-4-[(phenylmethyl)amino]-1-piperidinebutanamide and 120 parts of methanol was hydrogenated at normal pressure and at 50° C. with 2 parts of palladium-on-charcoal catalyst 10%. After the calculated amount of hydrogen was taken up, the catalyst was filtered off and the filtrate was evaporated, yielding 9 parts (98.9%) of [1(Y),-3B,trans]-4-amino-3-hydroxy-N,N,γ-trimethyl-α,α-diphenyl-1-piperidinebutanamide as a residue (interm. 32).

In a similar manner there was also prepared: [1(Y),-3A,trans]-4-amino-3-hydroxy-N,N,γ-trimethyl-α,α-diphenyl-1-piperidinebutanamide as a residue (interm. 33).

B. Preparation of Final Compounds

EXAMPLE 9

To a stirred and cooled solution of 4 parts of trans-4-amino-3-hydroxy-N,N,γ-trimethyl-α,αdiphenyl-1-piperidinebutanamide in 120 parts of trichloromethane were added 1.26 parts of N,N-diethylethanamine. A solution of 2.3 parts of 3-(trifluoromethyl)benzoyl chloride in 75 parts of trichloromethane was added dropwise. Upon completion, the reaction mixture was stirred overnight at room temperature. A solution of sodium carbonate in water was added. The separated organic layer was washed with water, dried, filtered and evaporated. The residue was taken up in 2,2'-oxybispropane. The precipitated product was filtered off and dried in vacuo at 60° C., yielding 4.9 parts (86.3%) of trans-3-hydroxy-N,N,γ-trimethyl-α,α-diphenyl-4-[[3-(trifluoromethyl)benzoyl]amino]-1-piperidinebutanamide; mp. 140.7° C. (compound 1).

In a similar manner there were also prepared:

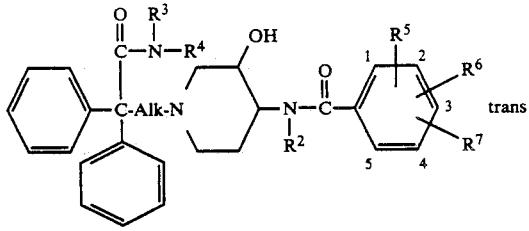

| No. | Alk | $R^3$ | $R^4$ | $R^2$ | $R^5, R^6, R^7$ | base/salt | mp. °C. |
|---|---|---|---|---|---|---|---|
| 2 | —CH$_2$—CH(CH$_3$)— | CH$_3$ | CH$_3$ | H | 2-Cl, 3-Cl | base | 187.9 |
| 3 | —CH$_2$—CH(CH$_3$)— | CH$_3$ | CH$_3$ | H | 2,3, 4-(OCH$_3$)$_3$ | base | 197.2 |
| 4 | —CH$_2$—CH(CH$_3$)— | CH$_3$ | CH$_3$ | H | 1-OH, 2-Cl, 3-Cl | base | 255.1 |
| 5 | —CH$_2$—CH(CH$_3$)— | CH$_3$ | CH$_3$ | H | 1-Cl, 5-Cl | base | 224.3 |
| 6 | —CH$_2$—CH(CH$_3$)— | CH$_3$ | CH$_3$ | H | 1-OH, 2-NO$_2$ | base | 247.4 |
| 7 | —CH$_2$—CH(CH$_3$)— | CH$_3$ | CH$_3$ | H | 2-Cl, 4-Cl | base | 203.0 |
| 8 | —CH$_2$—CH(CH$_3$)— | CH$_3$ | CH$_3$ | H | 1-Cl, 4-Cl | base | 225–230.7 |
| 9 | —CH$_2$—CH$_2$— | CH$_3$ | CH$_3$ | H | 2-CF$_3$ | hemihydrate | 149.1 |
| 10 | —CH$_2$—CH(CH$_3$)— | CH$_3$ | CH$_3$ | H | 2-Cl | base | 170.4 |
| 11 | —CH$_2$—CH(CH$_3$)— | 1-pyrrolidinyl | | H | 2-CF$_3$ | monohydrate | 129.8 |
| 12 | —CH$_2$—CH(CH$_3$)— | CH$_3$ | CH$_3$ | CH$_3$ | 2-CF$_3$ | base | 138.7 |
| 13 | —CH$_2$—CH(CH$_3$)— | 4-morpholinyl | | H | 2-CF$_3$ | base | 117.3 |
| 14 | —CH$_2$—CH(CH$_3$)— | CH$_3$ | CH$_3$ | H | 1-OH,3-Cl | base | 151.9 |
| 15 | —CH$_2$—CH(CH$_3$)— | CH$_3$ | CH$_3$ | H | 1-OH,4-NO$_2$ | hemihydrate | 201.3 |
| 16 | —CH$_2$—CH(CH$_3$)— | CH$_3$ | CH$_3$ | H | 1,3,5-(CH$_3$)$_3$ | base | 175.2 |
| 17 | —CH$_2$—CH(CH$_3$)— | CH$_3$ | CH$_3$ | H | 1-NO$_2$,2-Cl | base | 212.0 |
| 18 | —CH$_2$—CH(CH$_3$)— | CH$_3$ | CH$_3$ | H | 1-NO$_2$,3-Cl | base | 185.9 |
| 19 | —CH$_2$—CH(CH$_3$)— | CH$_3$ | CH$_3$ | H | 1-NO$_2$,3-F | base | 194.5 |
| 20 | —CH$_2$—CH(CH$_3$)— | CH$_3$ | CH$_3$ | H | 1-NO$_2$,2-OCH$_3$ | base | 214.0 |
| 21 | —CH$_2$—CH(CH$_3$)— | CH$_3$ | CH$_3$ | H | 1-NO$_2$,4-CH$_3$ | base | 227.5 |
| 22 | —CH$_2$—CH(CH$_3$)— | CH$_3$ | CH$_3$ | H | 3-CN | base | 148.7 |

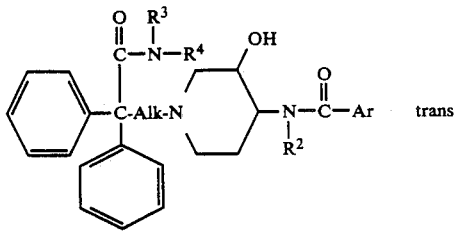

-continued

| No. | Alk | $R^3$ | $R^4$ | $R^2$ | Ar | base/salt | mp. °C |
|---|---|---|---|---|---|---|---|
| 23 | —CH$_2$—CH(CH$_3$)— | CH$_3$ | CH$_3$ | CH$_3$ | 3-pyridinyl | hemihydrate | 172.6 |
| 25 | —CH$_2$—CH(CH$_3$)— | CH$_3$ | CH$_3$ | H | 5-Br-2-furanyl | base | 167.2 |
| 26 | —CH$_2$—CH(CH$_3$)— | CH$_3$ | CH$_3$ | H | 2-thienyl | base | 181.3 |
| 27 | —CH$_2$—CH(CH$_3$)— | CH$_3$ | CH$_3$ | H | 4-thiazolyl | base | 179.9 |

In a similar manner there was also prepared: cis-3-hydroxy-N,N,γ-trimethyl-α,α-diphenyl-4-[[3-(trifluoromethyl)benzoyl]amino]-1-piperidinebutanamide ethanedioate(1:1); mp. 206.3° C. (compound 28).

EXAMPLE 10

To a stirred and cooled (ice bath) solution of 4 parts of 2-(phenylmethoxy)benzoic acid in 90 parts of trichloromethane were added first 1.47 parts of N,N-diethylethanamine and then 1.6 parts of ethyl carbonochloridate at <5° C. After stirring for 1 hour in an ice bath, the thus obtained mixture was added dropwise to a cooled solution of 5.94 parts of trans-4-amino-3-hydroxy-N,N,γ-trimethyl-α,α-diphenyl-1-piperidinebutanamide in 90 parts of trichloromethane at a temperature below 5° C. Upon completion, stirring was continued overnight at room temperature. The organic layer was washed with water, a sodium carbonate solution in water and water, dried, filtered and evaporated. The residue was purified by column chromatography over silica gel using a mixture of trichloromethane and methanol (95:5 by volume) as eluent. The pure fractions were collected and the eluent was evaporated. The residue was C solidified in 2,2'-oxybispropane. The product was filtered off and dried in vacuo at 60° C. yielding 3.7 parts (40.7%) of trans-3-hydroxy-N,N,γ-trimethyl-α,α-diphenyl-4-[[2(piperidinebutanamide: mp 149.0° C. (compound 29).

In a similar manner there were also prepared:

| No. | $R^3, R^4, R^5$ | mp. °C |
|---|---|---|
| 30 | 1-OCH$_3$, 3-Cl | 210.3 |
| 31 | 1-OCH$_3$, 2-Cl, 4-Cl | 171.4 |
| 32 | 1-OCH$_3$, 4-SO$_2$—NH$_2$ | 188.9 |
| 33 | 1-OCH$_3$, 3-NH—CH$_3$, 4-Cl | 191.8 |
| 34 | 2-CO-C$_3$H$_7$, 5-OCH$_3$ | 123.2 |
| 35 | 1-OC$_6$H$_5$ | 152.0 |
| 36 | 1-OCH$_2$—CH=CH$_2$, 3-Cl | 162.5 |
| 37 | 1-OCH$_3$, 3-SCH$_3$ | 195.0 |
| 38 | 1-Br, 2-NO$_2$ | 177.9 |
| 39 | 1-OCH$_3$, 3-NH—C(=O)—CH$_3$, 4-SCH$_3$ | 178.8 |

In a similar manner there were also prepared: trans-4-[[4-(acetylamino)-2-(acetyloxy)benzoyl]amino]-1-[4-(dimethylamino)-1-methyl-4-oxo-3,3-diphenylbutyl]-3-piperidinol acetate (ester); mp. 156.4° C. (compound 40); and trans-3-hydroxy-N,N,γ-trimethyl-α,α-diphenyl-4-[(3-thienyl)carbonylamino]-1-piperidinebutanamide hemihydrate; mp.194.4° C. (compound 41).

EXAMPLE 11

To a stirred solution of 3.95 parts of trans-4-amino-3-hydroxy-N,N,γ-trimethyl-α,α-diphenyl-1-piperidinebutanamide and 1.78 parts of 4-amino-5-cyano-2-hydroxybenzoic acid in 150 parts of trichloromethane were added 3.1 parts of N,N'-methanetetraylbis[cyclohexanamine] and stirring was continued over weekend at room temperature. The reaction mixture was acidified with an acetic acid solution in water. The separated organic layer was washed with water, dried, filtered and evaporated. The residue was taken up in acetonitrile and the precipitate was filtered off. The filtrate was purified by column chromatography over silica gel using a mixture of trichloromethane and methanol (90:10 by volume) as eluent. The pure fractions were collected and the eluent was evaporated. The residue was crystallized from acetonitrile. The product was filtered off and dried, yielding 0.55 parts (10%) of trans-4-[(4-amino-5-cyano-2-hydroxybenzoyl)amino]-3-hydroxy-N,N,γ-trimethyl-α,α-diphenyl-1-piperidinebutanamide monohydrate; mp. 211.4° C. (compound 42).

EXAMPLE 12

2.8 Parts of N,N-diethylethanamine were added to a solution of 1 part of 5H, 10H-diimidazo[1,5-a:1',5'-d]pyrazine-5,10-dione in 36 parts of N,N-dimethylformamide. The thus obtained suspension was added dropwise to a stirred and heated (70° C.) solution of 3.95 parts of trans-4-amino-3-hydroxy-N,N,γ-trimethyl-α,α-diphenyl-1-piperidinebutanamide in 18 parts of N,N-dimethylformamide. Upon complete addition, stirring was continued overnight at 70° C. After evaporation, the residue was purified by column chromatography over silica gel using a mixture of trichloromethane and methanol, saturated with ammonia, (90:10 by volume) as eluent. The pure fractions were collected and the eluent was evaporated. The residue was further purified by column chromatography (HPLC) over silica gel using a mixture of trichloromethane, methanol and methanol, saturated with ammonia, (90:9:1 by volume) as eluent. The pure fractions were collected and the eluent was evaporated. The residue was pulverised and evaporated again, yielding 1.13 parts (23%) of trans-3-hydroxy-4-[(1H-imidazol-5-yl)carbonylamino]-N,N,γ-trimethyl-α,α-diphenyl-1-piperidinebutanamide; mp. 155.0° C. (compound 43).

EXAMPLE 13

To a stirred and cooled (<5° C.) solution of 3.95 parts of trans-4-amino-3-hydroxy-N,N,γ-trimethyl-α,α-diphenyl-1-piperidinebuitanamide in 52 parts of trichloromethane was added dropwise a solution of 2.03 parts of 1-methyl-2H-3,1-benzoxazine-2,4(1H)dione in 48 parts of dichloromethane. Upon complete addition, the mixture was stirred for 32 hours at room temperature.

The separated organic layer was washed with a sodium hydroxide solution 5% in water and water, dried, filtered and evaporated. The residue was purified by column chromatography over silica gel using a mixture of trichloromethane and methanol (96:4 by volume) as eluent. The pure fractions were collected and the eluent was evaporated. The residue was dissolved in trichloromethane. The organic layer was washed with a sodium hydroxide solution 5% in water and water, dried, filtered and evaporated. The residue was crystallized from acetonitrile. The product was filtered off and dried in vacuo at 60° C., yielding 0.5 parts (9.4%) of trans-3-hydroxy-N,N,γ-trimethyl-4-[[2-(methylamino)-benzoyl]amino]-α,α-diphenyl-1-piperidinebutanamide; mp. 240.3° C. (compound 44).

EXAMPLE 14

To a stirred solution of 11.9 parts of trans-4-amino-3-hydroxy-,N,N,γ-trimethyl-α,α-diphenyl-1-piperidinebutanamide in 180 parts of trichloromethane was added a solution of 5.8 parts of 5-methoxy-2H-3,1-benzoxazine-2.4(1H)-dione in 45 parts of N,N-dimethylformamide at 50° C. Stirring was continued for 2 hours at 50° C. After evaporation, the residue was suspended in water. The product was filtered off and purified by column chromatography over silica gel using a mixture of trichloromethane and methanol, saturated with ammonia, (95:5 by volume) as eluent. The first fraction was collected and the eluent was evaporated. The residue was suspended in 2,2'-oxybispropane. The product was filtered off and dried, yielding a first fraction of 7.60 parts of trans-4-[(2-amino-6-methoxybenzoyl)amino]-3-hydroxy-N,N,γ-trimethyl-α,α-diphenyl-1-piperidinebutanamide. The second fraction was collected and the eluent was evaporated. The residue was crystallized from acetonitrile. The product was filtered off and dried, yielding a second fraction of 1.23 parts of trans-4-[(2-amino-6-methoxybenzoyl)amino]-3-hydroxy-N,N,γ-trimethyl-α,α-diphenyl-1-piperidinebutanamide. Total yield: 8.83 parts (54.1%) of trans-4-[(2-amino-6-methoxybenzoyl)amino]-3-hydroxy-N,N,γ-trimethyl-α,α-diphenyl-1-piperidinebutanamide; mp. 175.1° C. (compound 45).

In a similar manner there were also prepared:
trans-4-[(2-aminobenzoyl)amino]-3-hydroxy-N,N,γ-trimethyl-α,α-diphenyl-1-piperidinebutanamide monohydrate; mp. 164.5° C. (compound 46);

trans-4-[(2-amino-5-chlorobenzoyl)amino]-3-hydroxy-N,N,γ-trimethyl-α,α-diphenyl-1-piperidinebutanamide; mp. 183.1° C. (compound 47);

trans-4-[(2-amino-4-nitrobenzoyl)amino]-3-hydroxy-N,N,γ-trimethyl-α,α-diphenyl-1-piperidinebutanamide (compound 48); and trans-3-hydroxy-4-[[2-methoxy-6-(methylamino)benzoyl]amino]-N,N,γ-trimethyl-α,α-diphenyl-1-piperidinebutanamide; mp. 159.1° C. (compound 49).

EXAMPLE 15

A mixture of 4.5 parts of trans-4-amino-5-chloro-N-(3-hydroxy-4-piperidinyl)-2-methoxybenzamide, 4 parts of sodium carbonate, 0.1 parts of potassium iodide and 120 parts of 4-methyl-2-pentanone was stirred for 1 hour at reflux using a water separator. 5.95 Parts of N-(dihydro-5-methyl-3,3-diphenyl-2(3H)-furanylidene)-N-methylmethanaminium bromide were added and stirring was continued for 1 hour at reflux. The organic layer was washed successively with water, a sodium carbonate solution in water and water, dried, filtered and evaporated. The residue was purified by column chromatography over silica gel using a mixture of trichloromethane and methanol, saturated with ammonia, (98:2 by volume) as eluent. The pure fractions were collected and the eluent was evaporated. The residue was dried in vacuo at 80° C., yielding 2.66 parts (30.6%) of trans-4-[(4-amino-5-chloro-2-methoxybenzoyl)amino]-3-hydroxy-N,N,γ-trimethyl-α,α-diphenyl-1-piperidinebutanamide; mp. 131.9° C. (compound 50).

In a similar manner there was also prepared: cis-4-[(5-amino-4-chloro-2-methoxybenzoyl)amino]-3-methoxy-N,N,γ-trimethyl-α,α-diphenyl-1-piperidinebutanamide; mp. 191.1° C. (compound 51).

EXAMPLE 16

A mixture of 3.0 parts of trans-N-(3-methoxy-4-piperidinyl)-3-(trifluoromethyl)benzamide, 2.65 parts of sodium carbonate and 80 parts of 4-methyl-2-pentanone was stirred for 30 minutes at reflux temperature, using a water separator. After cooling 3.96 parts of N-(dihydro-5-methyl-3,3-diphenyl-2(3H)-furanylidene)-N-methylmethanaminium bromide were added and stirring was continued for 5 hours at reflux. After cooling overnight at room temperature, the reaction mixture was washed twice with 50 parts of water, dried, filtered and evaporated in vacuo. The residue was purified by column chromatography over silica gel using a mixture of trichloromethane and methanol (95:5 by volume) as eluent. The pure fractions were collected and the eluent was evaporated. The residue was crystallized from 8 parts of acetonitrile. The product was filtered off and dried, yielding 1.3 parts (22.5%) of trans-3-methoxy-N,N,γ-trimethyl-α,α-diphenyl-4-[[3-(trifluoromethyl)-benzoyl]amino]-1-piperidinebutanamide; mp. 197.8° C. (compound 52).

In a similar manner there was also prepared: trans-4-[(4-amino-5-chloro-2-methoxybenzoyl)amino]-3-methoxy-N,N,γ-trimethyl-α,α-diphenyl-1-piperidinebutanamide; mp. 184.8° C. (compound 53).

EXAMPLE 17

4.71 parts of cis-4-amino-5-chloro-2-methoxy-N-(3-methoxy-4-piperidinyl)benzamide, 3.66 parts of sodium carbonate, 0.1 parts of potassium iodide and 120 parts of 4-methyl-2-pentanone was stirred and refluxed for 15 minutes using a water separator. 6 parts of α-(2-bromopropyl)-N,N-dimethyl-α-phenylbenzeneacetamide were added and stirring was continued for 2.5 hours at reflux. Water was added. The organic layer was separated, washed with a sodium chloride solution, dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was suspended in 2,2'-oxybispropane. The product was filtered off and crystallized from acetonitrile, yielding 2.83 parts (31.8%) of cis-4-[(4-amino-5-chloro-2-methoxybenzoyl)amino]-3-methoxy-N,N,γ-trimethyl-α,α-diphenyl-1-piperidinebutanamide; mp. 198.3° C. (compound 54).

EXAMPLE 18

(a) To a stirred and cooled solution of 3.1 parts of (+)-(3A,trans)-4-amino-3-hydroxy-N,N,γ-trimethyl-α,α-diphenyl-1-piperidinebutanamide in 114 parts of trichloromethane and 0.94 parts of N,N-diethylethanamine was added dropwise a solution of 1.8 parts of 3-(trifluoromethyl)benzoyl chloride in 75 parts of trichloromethane. Upon completion, stirring was continued overnight at room temperature. The reaction mixture was washed with a sodium carbonate solution in water and water. The separated organic layer was dried, filtered and evaporated. The residue was solidified in 2,2'-oxybispropane and crystallized from a mixture of acetonitrile and 2,2'-oxybispropane. The product was filtered off and dried, yielding 1.3 parts (29.3%) of (−)-(3A,trans)-3-hydroxy-N,N,γ-trimethyl-α,α-diphenyl-4-[[3-(trifluoromethyl)benzoyl]amino]-1-piperidinebutanamide; mp. 197.7° C. $[\alpha]_{365}^{25} = -25.02°$ (c=1% in ethanol) (compound 55).

(b) 11.5 parts of (−)-(3A,trans)-3-hydroxy-N,N,γ-trimethyl-α, α-diphenyl-4-[[3-(trifluoromethyl)benzoyl]amino]-1-piperidinebutanamide were crystallized three times from acetonitrile. The product was filtered off and dried, yielding 6.7 parts (59.0%) of (−)-[1(X),3A,trans]-3-hydroxy-N,N,γ-trimethyl-α,α-diphenyl-4-[[3-(trifluoromethyl)benzoyl]amino]-1-piperidinebutanamide; mp. 215.1° C., $[\alpha]_{589}^{25} = -41.68°$ (c=1% in ethanol) (compound 56).

In a similar manner there were also prepared:
(+)-(3B,trans)-3-hydroxy-N,N,γ-trimethyl-α,α-diphenyl-4-[[3-(trifluoromethyl)benzoyl]amino]-1-piperidinebutanamide; mp. 205.9° C.;
$[\alpha]_{365}^{25} = +36.16°$ (c=1% in ethanol) (compound 57); and (+)-[1(X),3B,trans]-3-hydroxy-N,N,γ-trimethyl-α,α-diphenyl-4-[[3-(trifluoromethyl)benzoyl]amino]-1-piperidinebutanamide; mp. 215.0° C.;
$[\alpha]_{589}^{20} = +43.47°$ (c=1% in ethanol) (compound 58).

EXAMPLE 19

To a stirred and cooled (t<10° C.) solution of 9 parts of [1(Y),3B,trans[-4-amino-3-hydroxy-N,N,γ-trimethyl-α,α-diphenyl-1-piperidinebutanamide and 2.9 parts of N,N-diethylethanamine in 300 parts of trichloromethane was added dropwise a solution of 5.21 parts of 3-(trifluoromethyl)benzoyl chloride in 150 parts of trichloromethane. Upon completion, the reaction mixture was stirred for 3 hours at room temperature. The reaction mixture was washed with a sodium carbonate solution, dried, filtered and evaporated. The residue was purified by column chromatography over silica gel using a mixture of trichloromethane and methanol (95:5 by volume) as eluent. The pure fractions were collected and the eluent was evaporated. The residue was converted into the hydrochloride salt in 2-propanol. The salt was filtered off and dried for 48 hours in vacuo at 100° C., yielding 4.56 parts (32.8%) of (−)-[1(Y),3B,trans]-3-hydroxy-N,N,γ-trimethyl-α,α-diphenyl-4-[[3-(trifluoromethyl)benzoyl]amino]-1-piperidinebutanamide monohydrochloride; mp. 209.6° C.; $[\alpha]_{589}^{20} = -37.62°$ (c=1% in ethanol) (compound 59).

In a similar manner there was also prepared:
(+)-[1(Y),3A,trans]-3-hydroxy-N,N,γ-trimethyl-α,α-diphenyl-4-[[3-(trifluoromethyl)benzoyl]amino]-1-piperidinebutanamide; mp. 146.0° C., $[\alpha]_{589}^{25} = +21.44°$ (c=1% in ethanol) (compound 60).

EXAMPLE 20

To a stirred solution of 2.72 parts of trans-4-[(2-amino-6-methoxybenzoyl)amino]-3-hydroxy-N,N,γ-trimethyl-α,α-diphenyl-1-piperidinebutanamide in 20 parts of acetic acid were added 0.56 parts of acetic acid anhydride. After stirring overnight at room temperature, the reaction mixture was evaporated and the residue was purified by column chromatography over silica gel using a mixture of trichloromethane and methanol, saturated with ammonia, (95:5 by volume) as eluent. The pure fractions were collected and the eluent was evaporated. The residue was crystallized from 2,2'-oxybispropane. The product was filtered off and dried at 80° C., yielding 2.45 parts (83.5%) of trans-4-[[2-(acetylamino)-6-methoxybenzoyl]amino]-3-hydroxy-N,N,γ-trimethyl-α,α-diphenyl-1-piperidinebutanamide; mp. 146.5° C. (compound 61).

In a similar manner there were also prepared:
cis-4-[[5-(acetylamino)-2-methoxybenzoyl]amino]-3-methoxy-N,N,γ-trimethyl-α,α-diphenyl-1-piperidinebutanamide; mp. 122.9° C. (compound 62);
trans-4-[[4-(acetylamino)-2-methoxybenzoyl]amino]-3-hydroxy-N,N,γ-trimethyl-α,α-diphenyl-1-piperidinebutanamide; mp. 193.8° C. (compound 3); and
trans-4-[[4-(acetylamino)-5-chloro-2-methoxybenzoyl]amino]-3-hydroxy-N,N,γ-trimethyl-α,α-diphenyl-1-piperidinebutanamide; mp. 147.2° C. (compound 64).

EXAMPLE 21

To a stirred solution of 6.52 parts of cis-4-[(5-amino-4-chloro-2-methoxybenzoyl)amino]-3-methoxy-N,N,γ-trimethyl-α,α-diphenyl-1piperidinebutanamide in 195 parts of dichloromethane were added 2.6 parts of butanoyl chloride. After stirring for 15 minutes, 2.94 parts of N,N-diethylethanamine were added. The whole was stirred overnight at room temperature. The reaction mixture was washed successively with a sodium carbonate solution and water, dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was stirred in 2,2'-oxybispropane. The product was filtered off and dried, yielding 3.39 parts (46.5%) of cis-4-[[4-chloro-2-methoxy-5-[(1-oxobutyl)amino]benzoyl]amino]-3-methoxy-N,N,γ-trimethyl-α,α-diphenyl-1-piperidinebutanamide; mp. 130.7° C. (compound 65).

EXAMPLE 22

A mixture of 2.3 parts of trans-4-[(4-amino-2-methoxybenzoyl)amino]-3-hydroxy-N,N,γ-trimethyl-α,α-diphenyl-1-piperidinebutanamide, 2 parts of poly(oxymethylene), 1 part of a solution of thiophene in methanol 4% and 120 parts of methanol was hydrogenated at normal pressure and at 50° C. with 2 parts of palladium-on-charcoal catalyst 10%. After the calculated amount of hydrogen was taken up, the catalyst was filtered off and the filtrate was evaporated. The residue was crystallized from acetonitrile. The product was filtered off and dried in vacuo at 50° C., yielding 0.91 parts (39.7%) of trans-4-[[4-(dimethylamino)-2-methoxybenzoyl]amino]-3-hydroxy-N,N,γ-trimethyl-α,α-diphenyl-1-piperidinebutanamide; mp. 210.9° C. (compound 66).

EXAMPLE 23

A mixture of 4 parts of trans-4-[(4-fluoro-2-nitrobenzoyl)amino]-3-hydroxy-N,N,γ-trimethyl-α,α-diphenyl-1-piperidinebutanamide, 1 part of a solution of thiophene in methanol 4% and 200 parts of methanol was hydrogenated at normal pressure and at room temperature with 2 parts of platinum-on-charcoal catalyst 5%. After the calculated amount of hydrogen was taken up, the catalyst was filtered off and the filtrate was evaporated to dry. The residue was taken up In acetonitrile.

The organic layer was evaporated again and the residue was crystallized from a mixture of acetonitrile and a few drops of water. The product was filtered off and dried, yielding 1.93 parts (51.8%) of trans-4-[(2-amino-4-fluorobenzoyl)amino]-3-hydroxy-N,N,γ-trimethyl-α,α-diphenyl-1piperidinebutanamide monohydrate; mp. 127.0° C. (compound 67).

In a similar manner there were also prepared:

trans-4-[(3-amino-2-hydroxybenzoyl)amino]-3-hydroxy-N,N,γ-trimethyl-α,α-diphenyl-1-piperidinebutanamide; mp. 157.2° C. (compound 68);

trans-4-[(2-amino-3-chlorobenzoyl)amino]-3-hydroxy-N,N,γ-trimethyl-α,α-diphenyl-1-piperidinebutanamide; mp. 197.0° C. (compound 69);

trans-4-[(2-amino-4-chlorobenzoyl)amino]-3-hydroxy-N,N,γ-trimethyl-α,α-diphenyl 1-piperidinebutanamide monohydrate; mp. 130.9° C. (compound 70);

trans-4-[(2-amino-5-methylbenzoyl)amino]-3-hydroxy-N,N,γ-trimethyl-α,α-diphenyl-1-piperidinebutanamide; mp. 216.8° C. (compound 71);

trans-4-[(2,4-diaminobenzoyl)amino]-3-hydroxy-N,N,γ-trimethyl-α,α-diphenyl-1-piperidinebutanamide; mp. 136.1° C. (compound 72); and trans-4-[(2-amino-3-methoxybenzoyl)amino]-3-hydroxy-N,N,γ-trimethyl-α,α-diphenyl-1-piperidinebutanamide hemihydrate; mp. 169.5° C. (compound 73).

EXAMPLE 24

A mixture of 17.3 parts of cis-4-[(5-amino-4-chloro-2-methoxybenzoyl)amino]-3-methoxy-N,N,γ-trimethyl-α,α-diphenyl-1-piperidinebutanamide, 5 parts of calcium oxide and 250 parts of 2-methoxyethanol was hydrogenated at normal pressure and at 50° C. with 2 parts of palladium-on-charcoal catalyst 10%. After the calculated amount of hydrogen was taken up, the catalyst was filtered off and the filtrate was evaporated. The residue was purified by column chromatography over silica gel using a mixture of trichloromethane and methanol, saturated with ammonia, (95:5 by volume) as eluent. The pure fractions were collected and the eluent was evaporated. The residue was crystallized from acetonitrile. The product was filtered off and dried, yielding 16.2 parts (100%) of cis-4[(5-amino-2-methoxybenzoyl)amino]-3-methoxy-N,N,γ-trimethyl-αα-diphenyl-1-piperidinebutanamide; mp. 189.0° C. (compound 74).

In a similar manner there were also prepared:

trans-4[(4-amino-2-methoxybenzoyl)amino]-3-hydroxy-N,N,γ-trimethyl-α,α-diphenyl-1-piperidinebutanamide; mp. 212.5° C. (compound 75); and cis-4-[(4-amino-2-methoxybenzoyl)amino]-3-hydroxy-N,N,γ-trimethyl-α,α-diphenyl-1-piperidinebutanamide: mp. 151.2° C. (compound 76).

EXAMPLE 25

A mixture of 2.7 parts of trans-3-hydroxy-N,N,γ-trimethyl-α,α-diphenyl-4-[[2-(phenylmethoxy)benzoyl]amino]-1-piperidinebutanamide and 120 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was purified by column chromatography over silica gel using a mixture of trichloromethane and methanol (95:5 by volume) as eluent. The pure fractions were collected and the eluent was evaporated. The residue was taken up in methylbenzene and the solvent was evaporated again. The residue was suspended in a mixture of 2,2'-oxybispropane and a few drops of acetonitrile. The product was filtered off and dried in vacuo at 70° C., yielding 1.3 parts (63.0%) of trans-3-hydroxy-4-[(2-hydroxybenzoyl)-amino]-N,N,γ-trimethyl-α,α-diphenyl-1-piperidinebutanamide; mp. 154.3° C. (compound 77).

C. Pharmacological Examples

The useful pharmacological properties of the compounds of formula (1) and their pharmacological acceptable acid-addition salts can be demonstrated by the "Ricinus Oil Test" and by the "Tail Withdrawal Test".

EXAMPLE 26

Ricinus Oil Test in Rats

Female Wistar rats were fasted overnight. Each animal was treated orally with a dose level of the compound to be tested. One hour thereafter, the animal received 1 ml of ricinus oil orally. Each animal was kept in an individual cage and 1 hour after the ricinus oil treatment, the presence or absence of diarrhea was noted. The $ED_{50}$ value was determined as that dose in mg/kg body weight, at which no diarrhea was present in 50% of the tested animals. Said $ED_{50}$-values for the compounds of the present invention can be found in the first column of Table 1.

EXAMPLE 27

Tail Withdrawal Test

Male Wistar rats were fasted overnight. Each animal was treated orally with a dose level of the compound to be tested. The thus treated rats Were put into individual restraining cages. At various time periods after administration, the lower 5 cm portion of the tail was immersed into a cup filled with water at a constant temperature of 55° C. The typical tail withdrawal response was evaluated during a 10 seconds period after the immersion. $ED_{50}$ values in mg/kg body weight were determined as that dose of the test compound capable of suppressing in 50% of the tested animals the typical tail withdrawal response during a time period exceeding 10 seconds. Said $ED_{50}$ values obtained for the compounds of the present invention are gathered in Table 1 column two.

TABLE 1

| Comp. No. | Ricinus Oil Test $ED_{50}$ in mg/kg body weight | Tail Witdrawal Test $ED_{50}$ in mg/kg body weight |
|---|---|---|
| 50 | 2.5 | >40 |
| 53 | 2.5 | ~40 |
| 75 | 2.5 | >40 |
| 2 | 0.63 | >160 |
| 5 | 0.31 | ≧40 |
| 1 | 0.15 | >160 |
| 68 | 0.63 | >40 |
| 7 | 0.31 | >40 |
| 30 | 0.63 | ≧40 |
| 31 | 0.63 | ~40 |
| 47 | 0.08 | ~40 |
| 10 | 0.04 | >40 |
| 34 | <2.5 | >40 |
| 52 | 2.5 | 40 |
| 29 | ≦0.63 | ~40 |
| 77 | 0.16 | ≧40 |
| 64 | 2.5 | >40 |
| 38 | 2.5 | >40 |
| 17 | 0.63 | >40 |
| 69 | <0.63 | >40 |
| 19 | 1.25 | >40 |

TABLE 1-continued

| Comp. No. | Ricinus Oil Test ED$_{50}$ in mg/kg body weight | Tail Witdrawal Test ED$_{50}$ in mg/kg body weight |
| --- | --- | --- |
| 67 | <0.04 | >40 |
| 70 | <0.63 | >40 |
| 21 | ≦0.63 | >40 |
| 57 | 0.31 | >160 |
| 55 | 1.0 | >160 |

(D) Composition Examples

The following formulations exemplify typical pharmaceutical compositions in dosage unit form suitable for systemic administration to animal and human subjects in accordance with tbe instant invention. "Active ingredient" (A.I.) as used throughout these examples relates to a compound of formula (I) or a pharmaceutically acceptable acid addition salt thereof.

EXAMPLE 28 : ORAL DROPS 500 g of the A.1. was dissolved in 0.5 l of 2-hydroxypropanoic acid and 1.5 l of the polyethylene glycol at 60°~80° C. After cooling to 30°~40° C. there were added 35 l of polyethylene glycol and the mixture was stirred Well. Then there was added a solution of 1750 g of sodium saccharin in 2.5 l of purified water and while stirring there were added 2.5 l of cocoa flavor and polyethylene glycol q.s. to a volume of 50 l, providing an oral drop solution comprising 10 mg of the A.I. per ml. The resulting solution was filled into suitable containers.

EXAMPLE 29 : ORAL SOLUTION 9 g of methyl 4-hydroxybenzoate and 1 g of propyl 4-hydroxy-benzoate were dissolved in 4 l of boiling purified water. In 3 l of this solution were dissolved first 10 9 of 2,3-dihydroxybutanedioic acid and thereafter 20 g of the A.1. The latter solution was combined with the remaining part of the former solution and 12 1 1,2,3-propane-triol and 3 l of sorbitol 70% solution were added thereto. 40 g of sodium saccharin were dissolved in 0.5 l of water and 2 ml of raspberry and 2 ml of gooseberry essence were added. The latter solution was combined with the former, water was added q.s. to a volume of 20 l providing an oral solution comprising 20 mg of the active ingredient per teaspoonful (5 ml). The resulting solution was filled in suitable containers.

EXAMPLE 30 : CAPSULES 20 9 of the A.I., 6 g sodium lauryl sulfate, 56 g starch. 56 g lactose. 0.B g colloidal silicon dioxide, and 1.2 g magnesium stearate were vigorously stirred together. The resulting mixture was subsequently filled into 1000 suitable hardened gelatin capsules, comprising each 20 mg of the active ingredient.

EXAMPLE 31:FILM-COATED TABLETS

Preparation of tablet core

A mixture of 100 g of the A.1., 570 g lactose and 200 g starch was mixed well and thereafter humidified with a solution of 5 g sodium dodecyl sulfate and 10 g polyvinylpyrrolidone (Kollidon-K 90 ®) in about 200 ml of water. The wet powder mixture was sieved, dried and sieved again. Then there was added 100 g microcrystalline cellulose (Avicel ®) and 15 g hydrogenated vegetable oil (Sterotex ®). The whole was mixed well and compressed into tablets, giving 10.000 tablets, each containing 10 mg of the active ingredient.

Coating

15 To a solution of 10 9 methyl cellulose (Methocel 60 HG ®) in 75 ml of denatured ethanol there was added a solution of 5 g of ethyl cellulose (Ethocel 22 cps ®) in 150 ml of dichloromethane. Then there were added 75 ml of dichloromethane and 2.5 ml 1,2.3-propane-triol. 10 g of polyethylene 9lycol was molten and dissolved in 75 ml of 20 dichloromethane. The latter solution was added to the former and then there were added 2.5 g of magnesium octadecanoate, 5 g of polyvinylpyrrolidone and 30 ml of concentrated colour suspension (Opaspray K-1-2109 ®) and the whole was homogenated. The tablet cores were coated with the thus obtained mixture in a coating 25 apparatus.

EXAMPLE 32 : INJECTABLE SOLUTION 1.8 g methyl 4-hydroxybenzoate and 0.2 g propyl 4-hydroxybenzoate were dissolved in about 0.5 l of boiling water for injection. After cooling to about 50° C there were added while stirring 4 g lactic acid, 0.05 g propylene glycol and 4 g of the A.I. The solution was cooled to room temperature and supplemented with water for injection q.s. ad 1 l volume, giving a solution of 4 m9 A.I. per ml. The solution was sterilized by filtration (U.S.P. XVII p. 811) and 35 filled in sterile containers.

EXAMPLE 33: SUPPOSITORIES 3 g A.1. was dissolved in a solution of 3 g 2,3-dihydroxybutanedioic acid in 25 ml polyethylene glycol 400. 12 g Surfactant (SPAN ®) and triglycerides (Witepsol 555 ®) q.s. ad 300 g were molten together. The latter mixture was mixed well with the former solution. The thus obtained mixture was poured into moulds at a temperature of 37°~38° C. to form 100 suppositories each containing 30 mg of the active ingredient.

What is claimed is:

1. A method of treating warm-blooded animals suffering from diarrhea, which method comprises the systemic administration to warm-blooded animals of an amount effective in treating diarrhea of a compound having the formula:

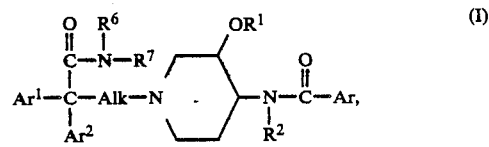

an N-oxide form, a pharmaceutically acceptable acid-solution salt, or a possible stereoisomeric form thereof, wherein R$^1$ is a member selected from the group consisting of hydrogen, C$_{1-6}$alkyl, aryl C$_{1-6}$alkyl; C$_{1-6}$alkylcarbonyl, aminoC$_{1-6}$alkyl, and mono- and di(C$_{1-6}$alkyl)aminoC$_{1-6}$alkyl;

R$^2$ is a member selected from the group consisting of hydrogen and C$_{1-6}$alkyl;

Ar is a radical of the formula;

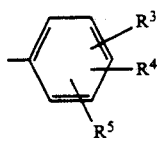
(a-1)

wherein $R^3$, $R^4$, and $R^5$ are each independently selected from the group consisting of hydrogen, $C_{1-6}$alkyl, $C_{1-6}$alkyloxy, halo, hydroxy, cyano, nitro, amino, mono- and di($C_{1-6}$alkyl)amino, aminocarbonyl, arylcarbonylamino, $C_{1-6}$alkylcarbonylamino, $C_{1-6}$alkylcarbonyl, $C_{1-6}$alkylcarbonyloxy, aminosulfonyl, $C_{1-6}$alkylsulfinyl, $C_{1-6}$alkylsulfonyl, $Cl-6$ alkylthio, mercapto, $C3-6$ alkynyloxy, $C3-6$ alkenyloxy, aryl $C_{1-6}$alkyloxy, aryloxy, and $C_{1-6}$alkyl substituted with up to 4 halo atoms;

Alk is $-CH_2-CH_2-$ or $-CH_2-CH(CH_3)-$;

$Ar^1$ and $Ar^2$ are, each independently, phenyl or halophenyl;

$R^6$ and $R^7$ are each independently hydrogen, $C_{1-6}$alkyl, phenylmethyl, or 2-propenyl;

wherein aryl is member selected from the group consisting of phenyl being optionally substituted with up to 3 substituents each independently selected from the group consisting of halo, hydroxy, $C_{1-6}$alkyl, $C_{1-6}$alkyloxy, aminosulfonyl, $C_{1-6}$alkylcarbonyl, nitro, trifluoromethyl, amino, aminocarboxyl, and phenylcarbonyl, said phenylcarbonyl being optionally substituted with up to 3 halo atoms.

2. A method according to claim 1 wherein the active compound is a compound of formula (I) wherein the substituents in the 3- and 4-position of the piperidine ring have the trans configuration.

3. A method according to claim 2 wherein Ar is a radical of formula (a-1) wherein $R^3$ is aryl$C_{1-6}$alkyloxy, aryloxy, $C_{3-6}$alkenyloxy, $C_{3-6}$alkynyloxy, and $C_{1-4}$alkyl substituted with up to 4 halo atoms, and $R^4$ and $R^5$ are each independently selected from the group consisting of hydrogen, $C_{1-6}$alkyl$C_{1-6}$alkyloxy, halo, hydroxy, cyano, nitro, amino, mono- and di($C_{1-6}$alkyl)amino, aminocarbonyl, arylcarbonylamino, $C_{1-6}$alkylcarbonylamino, $C_{1-6}$alkylcarbonyl, $C_{1-6}$alkylcarbonyloxy, aminosulfonyl, $C_{1-6}$alkylsulfinyl, $C_{1-6}$alkylsulfonyl, $C_{1-6}$alkylthio, mercapto, aryl $C_{1-6}$alkyloxy, aryloxy, $C_{3-6}$alkenyloxy, $C_{3-6}$alkynyloxy, and $C_{1-6}$alkyl substituted with up to 4 halo atoms.

4. A method according to claim 2 wherein Ar is a radical of formula (a-1) wherein $R^3$, $R^4$, and $R^5$ are each independently selected from the group consisting of hydrogen, $C_{1-6}$alkyl, $C_{1-6}$alkyloxy, halo, hydroxy, cyano, nitro, amino, mono- and di(($C_{1-6}$alkyl)amino, aminocarbonyl, arylcarbonylamino, $C_{1-6}$alkylcarbonylamino $C_{1-6}$alkycarbonyl, $C_{1-6}$alkylcarbonyloxy, aminosulfonyl, $C_{1-6}$alkylsulfinyl $C_{1-6}$alkylsulfonyl $C_{1-6}$alkylthio, and mercapto.

5. A method according to claim 3 wherein Ar is a radical of formula (a-1) wherein $R^3$ is phenylmethoxy, phenyloxy, propenyloxy, or $C_{1-4}$alkyl substituted with up to 4 halo substituents, and $R^4$ and $R^5$ are each independently hydrogen, $C_{1-4}$alkyl, $C_{1-4}$alkyloxy, halo, hydroxy, nitro, amino, phenylmethoxy, phenoxy, propenyloxy, or $C_{1-4}$alkyl substituted with up to 4 halo atoms; $R^1$ is hydrogen or $C_{1-4}$alkyl; and $R^6$ and $R^7$ are each independently hydrogen, $C_{1-4}$alkyl, phenylmethyl, or 2-propenyl.

6. A method according to claim 5 wherein Ar is a radical of formula (a-1) wherein $R^3$ is trifluoromethyl substituted on the meta position and $R^4$ and $R^5$ are each independently hydrogen, methyl, methoxy, halo, hydroxy, nitro, amino, trifluoromethyl, phenylmethoxy, phenoxy, or propenyloxy.

7. A method according to claim 1, wherein $R^3$ is $C_{1-6}$alkyl substituted with 1–4 halo atoms.

8. An anti-diarrheal composition comprising an inert carrier and as an active ingredient an anti-diarrheal amount of at least one compound having the formula:

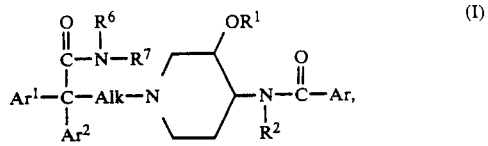
(I)

an N-oxide form, a pharmaceutically acceptable acid-addition salt, or a possible stereoisomeric form thereof, wherein $R^1$ is a member selected from the group consisting of hydrogen, $C_{1-6}$alkyl, acryl $C_{1-6}$alkyl, $C_{1-6}$alkylcarbonyl, amino $C_{1-6}$alkyl, and mono- and di-($C_{1-6}$alkyl)amino $C_{1-6}$alkyl;

$R^2$ is a member selected from the group consisting of hydrogen and $C_{1-6}$alkyl;

Ar is a radical of the formula:

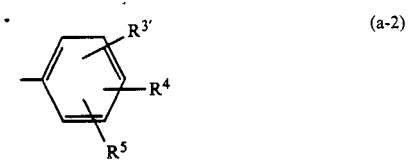
(a-2)

wherein $R^3$, is aryl $C_{1-6}$alkyloxy, aryloxy, $C_{3-6}$alkenyloxy, $C_{3-6}$alkynyloxy, or $C_{1-5}$alkyl substituted with 1-4 halo atoms, and $R^4$ and $R^5$ are each independently selected from the group consisting of hydrogen, $C_{1-6}$alkyl, $C_{1-6}$alkyloxy, halo, hydroxy, cyano, nitro, amino, mono- and di ($C_{1-6}$alkyl)amino, aminocarbonyl, arylcarbonylamino, $C_{1-6}$alkylcarbonylamino, $C_{1-6}$alkylcarbonyl, $C_{1-6}$alkylcarbonyloxy, aminosulfonyl, $C_{1-6}$alkylsulfinyl, $C_{1-6}$alkylsulfonyl, $C_{1-6}$alkylthio, mercapto, $C_{3-6}$alkynyloxy, $C_{3-6}$alkenyloxy, aryl $C_{1-6}$alkyloxy, aryloxy, and $C_{1-6}$alkyl substituted with up to 4 halo atoms;

Alk is $-CH_2-CH_2-$or $-CH_2-CH(CH_3)-$;

$Ar^1$ and $Ar^2$ are each independently phenyl or halophenyl;

$R^6$ and $R^7$ are each independently hydrogen, $C_{1-6}$alkyl, phenylmethyl, or 2-propenyl;

wherein aryl is a member selected from the group consisting of phenyl being optionally substituted with up to 3 substituents each independently selected from the group consisting of halo, hydroxy, $C_{1-6}$alkyl, $C_{1-6}$alkyloxy, aminosulfonyl, $C_{1-6}$alkylcarbonyl, nitro, trifluoromethyl, amino, aminocarbonyl and phenylcarbonyl, said phenylcarbonyl being optionally substituted with up to 3 halo atoms.

9. An anti-diarrheal composition according to claim 8 wherein the active compound is a compound of formula (I) wherein the substituents in the 3- and 4-position of the piperidine ring have the trans configuration.

10. An anti-diarrheal composition according to claim 9 wherein Ar is a radical of formula (a-2) wherein $R^4$ and $R^5$ are each independently selected from the group consisting of hydrogen, $C_{1-6}$alkyl, $C_{1-6}$alkyloxy, halo, hydroxy, cyano, nitro, amino, mono- and di($C_{1-6}$alkyl)amino, aminocarbonyl, arylcarbonylamino, $C_{1-6}$alkylcarbonylamino, $C_{1-6}$alkylcarbonyl, $C_{1-6}$alkylcarbonyloxy, aminosulfonyl, $C_{1-6}$alkylsulfinyl, $C_{1-6}$alkylsulfonyl, $C_{1-6}$alkylthio, and mercapto.

11. An anti-diarrheal composition according to claim 9 wherein Ar is a radical of formula (a-2) wherein $R^3$ is phenylmethoxy, phenyloxy, propenyloxy, or $C_{1-4}$alkyl substituted with up to 4 halo substituents; $R^4$ and $R^5$ are each independently hydrogen, $C_{1-4}$alkyl, $C_{1-4}$alkyloxy, halo, hydroxy, nitro, amino, phenylmethoxy, phenoxy, propenyloxy, or $C_{1-4}$alkyl substituted with up to 4 halo atoms; $R^1$ is hydrogen or $C_{1-4}$alkyl; and $R^6$ and $R^7$ are each independently hydrogen, $C_{1-4}$alkyl, phenylmethyl, or 2-propenyl.

12. An anti-diarrheal composition according to claim 11 wherein Ar is a radical of formula (a-2) wherein $R^3$, is trifluoromethyl substituted on the meta position, and $R^4$ and $R^5$ are each independently hydrogen, methyl, methoxy, halo, hydroxy, nitro, amino, trifluoromethyl, phenylmethoxy, phenoxy, or propenyloxy.

13. An anti-diarrheal composition according to claim 8 wherein the compound is that wherein $R^{3'}$ is $C_{1-6}$alkyl substituted with 1-4 halo atoms.

14. A method according to claim 1 wherein the compound is trans-3-hydroxy-N,N,$\gamma$-trimethyl-$\alpha\alpha$-diphenyl-4-[[3-(trifluoromethyl)-benzoyl]amino]-1-piperidinebutanamide.

15. An anti-diarrheal composition according to claim 8 wherein the compound is trans-3-hydroxy-N,N,$\gamma$-trimethyl-$\alpha,\alpha$-diphenyl-4-[[3-(trifluoromethyl)benzoyl]amino]-1-piperidinebutanamide.

* * * * *

UNITED STATES PATENT AND TRADEMARK OFFICE
CERTIFICATE OF CORRECTION

PATENT NO. : 4,990,521
DATED : February 5, 1991
INVENTOR(S) : Van Daele et al.

It is certified that error appears in the above-identified patent and that said Letters Patent is hereby corrected as shown below:

Claim 1, column 30, line 59 "solution" should be ---addition---.

Claim 12, column 34, line 2 "$R^3$" should be ---$R^{3'}$---.

Claim 14, line 11 "$\alpha\alpha$" should be ---$a, \alpha$---.

Signed and Sealed this

Thirteenth Day of October, 1992

Attest:

DOUGLAS B. COMER

*Attesting Officer*    Acting Commissioner of Patents and Trademarks